(12) United States Patent
Bachmann et al.

(10) Patent No.: US 10,835,600 B2
(45) Date of Patent: Nov. 17, 2020

(54) COMPOSITIONS AGAINST CAT ALLERGY

(71) Applicant: UNIVERSITÄT ZÜRICH, Zürich (CH)

(72) Inventors: Martin Bachmann, Rämismühle (CH); Gary Jennings, Zürich (CH); Thomas Kündig, Zürich (CH); Gabriela Senti, Stäfa (CH); Franziska Zabel, Lucerne (CH)

(73) Assignee: UNIVERSITÄT ZÜRICH, Zürich (CH)

( * ) Notice: Subject to any disclaimer, the term of this patent is extended or adjusted under 35 U.S.C. 154(b) by 45 days.

(21) Appl. No.: 15/758,049

(22) PCT Filed: Sep. 7, 2016

(86) PCT No.: PCT/EP2016/071125
§ 371 (c)(1),
(2) Date: Mar. 7, 2018

(87) PCT Pub. No.: WO2017/042241
PCT Pub. Date: Mar. 16, 2017

(65) Prior Publication Data
US 2018/0250387 A1 Sep. 6, 2018

(30) Foreign Application Priority Data

Sep. 8, 2015 (EP) .................................... 15184198
Oct. 13, 2015 (EP) .................................... 15189558

(51) Int. Cl.
*A61K 39/35* (2006.01)
*A61K 39/00* (2006.01)

(52) U.S. Cl.
CPC ...... *A61K 39/35* (2013.01); *A61K 2039/5258* (2013.01); *A61K 2039/6037* (2013.01); *A61K 2039/6075* (2013.01)

(58) Field of Classification Search
None
See application file for complete search history.

(56) References Cited

U.S. PATENT DOCUMENTS

2004/0076611 A1* 4/2004 Bachmann ............. A61K 39/00
424/93.2

FOREIGN PATENT DOCUMENTS

WO 2006/097530 A2 9/2006
WO 2007/113633 A2 10/2007

OTHER PUBLICATIONS

International Search Report in International Application No. PCT/EP2016/071125, dated Nov. 16, 2016.
(Continued)

*Primary Examiner* — M Franco G Salvoza
(74) *Attorney, Agent, or Firm* — Medler Ferro Woodhouse & Mills PLLC

(57) ABSTRACT

The present invention relates to the use of a composition in a method of reducing the allergenicity of a cat. Moreover, the present invention relates to the use of a composition in a method of reducing the allergenicity of a cat for a human exposed to the cat. Furthermore, the present invention relates to compositions comprising a virus-like particle (VLP) and at least one Fel d1 protein. The compositions of the invention induce efficient immune responses, in particular antibody responses, in cats and are useful for the treatment and/or prevention of cat allergy.

Figure 1:
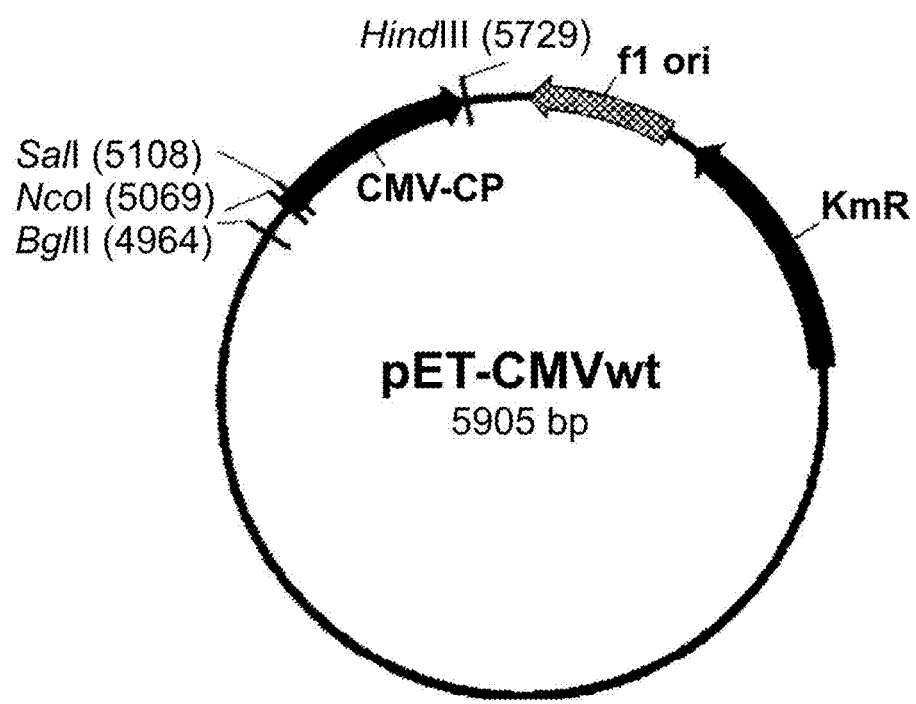

20 Claims, 18 Drawing Sheets
Specification includes a Sequence Listing.

(56) References Cited

OTHER PUBLICATIONS

Plummer E M et al., "Viral nanoparticles and virus-like particles: platforms for contemporary vaccine design," WIREs Nanomedicine and Nanobiotechnology 3:174-196 (2011).

* cited by examiner

SEQUENCE LISTING

```
<160> NUMBER OF SEQ ID NOS: 34

<210> SEQ ID NO 1
<211> LENGTH: 218
<212> TYPE: PRT
<213> ORGANISM: cucumber mosaic virus

<400> SEQUENCE: 1
```

Met Asp Lys Ser Glu Ser Thr Ser Ala Gly Arg Ser Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
                100                 105                 110

Pro Leu Pro Lys Phe Asp Ser Thr Val Trp Val Thr Val Arg Lys Val
            115                 120                 125

Pro Ala Ser Ser Asp Leu Ser Val Ala Ala Ile Ser Ala Met Phe Ala
        130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
                180                 185                 190

Ala Leu Glu Thr Asp Glu Leu Val Leu His Val Asp Val Glu His Gln
            195                 200                 205

Arg Ile Pro Thr Ser Gly Val Leu Pro Val
        210                 215

<210> SEQ ID NO 2
<211> LENGTH: 217
<212> TYPE: PRT
<213> ORGANISM: cucumber mosaic virus

<400> SEQUENCE: 2

Asp Lys Ser Glu Ser Thr Ser Ala Gly Arg Asn Arg Arg Arg Pro
1               5                   10                  15

Arg Arg Gly Ser Arg Ser Ala Ser Ser Ala Asp Ala Asn Phe Arg
            20                  25                  30

Val Leu Ser Gln Gln Leu Ser Arg Leu Asn Lys Thr Leu Ala Ala Gly
        35                  40                  45

Arg Pro Thr Ile Asn His Pro Thr Phe Val Gly Ser Glu Arg Cys Lys
    50                  55                  60

Pro Gly Tyr Thr Phe Ser Ser Ile Thr Leu Lys Pro Pro Lys Ile Asp
65                  70                  75                  80

Arg Gly Ser Tyr Tyr Gly Lys Arg Leu Leu Leu Pro Asp Ser Val Thr
                85                  90                  95

Glu Phe Asp Lys Lys Leu Val Ser Arg Ile Gln Ile Arg Val Asn Pro
                100                 105                 110

Leu Pro Lys Phe Asp Ser Thr Val Trp Val Thr Val Arg Lys Val Pro
            115                 120                 125

Ala Ser Ser Asp Leu Ser Val Ala Ala Ile Ser Ala Met Phe Ala Asp
        130                 135                 140

Gly Ala Ser Pro Val Leu Val Tyr Gln Tyr Ala Ala Ser Gly Val Gln

```
                145                 150                 155                 160

Ala Asn Asn Lys Leu Leu Tyr Asp Leu Ser Ala Met Arg Ala Asp Ile
                    165                 170                 175

Gly Asp Met Arg Lys Tyr Ala Val Leu Val Tyr Ser Lys Asp Asp Ala
                180                 185                 190

Leu Glu Thr Asp Glu Leu Val Leu His Val Asp Ile Glu His Gln Arg
                    195                 200                 205

Ile Pro Thr Ser Gly Val Leu Pro Val
    210                 215

<210> SEQ ID NO 3
<211> LENGTH: 218
<212> TYPE: PRT
<213> ORGANISM: cucumber mosaic virus

<400> SEQUENCE: 3

Met Asp Lys Ser Glu Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
                20                  25                  30

Arg Ala Leu Thr Gln Gln Met Leu Lys Leu Asn Lys Thr Leu Ala Ile
                35                  40                  45

Gly Arg Pro Thr Leu Asn His Pro Thr Phe Val Gly Ser Ala Ser Cys
            50                  55                  60

Lys Pro Gly Tyr Thr Phe Thr Ser Ile Thr Leu Lys Pro Pro Glu Ile
65                  70                  75                  80

Glu Lys Gly Ser Tyr Phe Gly Arg Arg Leu Ser Leu Pro Asp Ser Val
                85                  90                  95

Thr Asp Tyr Asp Lys Lys Leu Val Ser Arg Ile Gln Ile Arg Ile Asn
                    100                 105                 110

Pro Leu Pro Lys Phe Asp Ser Thr Val Trp Val Thr Val Arg Lys Val
                115                 120                 125

Pro Ser Ser Ser Asp Leu Ser Val Ala Thr Ile Ser Ala Met Phe Gly
            130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                    165                 170                 175

Ile Gly Asp Met Arg Lys Tyr Ala Val Leu Val Tyr Ser Lys Asp Asp
                180                 185                 190

Lys Leu Glu Glu Asp Glu Ile Val Leu His Val Asp Val Glu His Gln
                    195                 200                 205

Arg Ile Pro Ile Ser Arg Met Leu Pro Thr
    210                 215

<210> SEQ ID NO 4
<211> LENGTH: 14
<212> TYPE: PRT
<213> ORGANISM: artificial sequence
<220> FEATURE:
<223> OTHER INFORMATION: tetanus toxoid epitope tt830

<400> SEQUENCE: 4

Gln Tyr Ile Lys Ala Asn Ser Lys Phe Ile Gly Ile Thr Glu
1               5                   10

<210> SEQ ID NO 5
```

```
<211> LENGTH: 13
<212> TYPE: PRT
<213> ORGANISM: artificial sequence
<220> FEATURE:
<223> OTHER INFORMATION: PADRE

<400> SEQUENCE: 5

Ala Lys Phe Val Ala Ala Trp Thr Leu Lys Ala Ala Ala
1               5                   10

<210> SEQ ID NO 6
<211> LENGTH: 222
<212> TYPE: PRT
<213> ORGANISM: artificial sequence
<220> FEATURE:
<223> OTHER INFORMATION: CMV-Ntt830

<400> SEQUENCE: 6

Met Gly Gln Tyr Ile Lys Ala Asn Ser Lys Phe Ile Gly Ile Thr Glu
1               5                   10                  15

Arg Arg Arg Arg Pro Arg Gly Ser Arg Ser Ala Pro Ser Ser Ala
            20                  25                  30

Asp Ala Asn Phe Arg Val Leu Ser Gln Gln Leu Ser Arg Leu Asn Lys
            35                  40                  45

Thr Leu Ala Ala Gly Arg Pro Thr Ile Asn His Pro Thr Phe Val Gly
        50                  55                  60

Ser Glu Arg Cys Lys Pro Gly Tyr Thr Phe Thr Ser Ile Thr Leu Lys
65                  70                  75                  80

Pro Pro Lys Ile Asp Arg Gly Ser Tyr Tyr Gly Lys Arg Leu Leu Leu
                85                  90                  95

Pro Asp Ser Val Thr Glu Tyr Asp Lys Lys Leu Val Ser Arg Ile Gln
            100                 105                 110

Ile Arg Val Asn Pro Leu Pro Lys Phe Asp Ser Thr Val Trp Val Thr
        115                 120                 125

Val Arg Lys Val Pro Ala Ser Ser Asp Leu Ser Val Ala Ala Ile Ser
    130                 135                 140

Ala Met Phe Ala Asp Gly Ala Ser Pro Val Leu Val Tyr Gln Tyr Ala
145                 150                 155                 160

Ala Ser Gly Val Gln Ala Asn Asn Lys Leu Leu Tyr Asp Leu Ser Ala
                165                 170                 175

Met Arg Ala Asp Ile Gly Asp Met Arg Lys Tyr Ala Val Leu Val Tyr
            180                 185                 190

Ser Lys Asp Asp Ala Leu Glu Thr Asp Glu Leu Val Leu His Val Asp
        195                 200                 205

Val Glu His Gln Arg Ile Pro Thr Ser Gly Val Leu Pro Val
    210                 215                 220

<210> SEQ ID NO 7
<211> LENGTH: 220
<212> TYPE: PRT
<213> ORGANISM: artificial sequence
<220> FEATURE:
<223> OTHER INFORMATION: CMV-Npadr

<400> SEQUENCE: 7

Met Ala Lys Phe Val Ala Ala Trp Thr Leu Lys Ala Ala Ala Arg Arg
1               5                   10                  15

Arg Arg Pro Arg Arg Gly Ser Arg Ser Ala Pro Ser Ser Ala Asp Ala
            20                  25                  30
```

```
Asn Phe Arg Val Leu Ser Gln Gln Leu Ser Arg Leu Asn Lys Thr Leu
             35                  40                  45

Ala Ala Gly Arg Pro Thr Ile Asn His Pro Thr Phe Val Gly Ser Glu
 50                  55                  60

Arg Cys Lys Pro Gly Tyr Thr Phe Thr Ser Ile Thr Leu Lys Pro Pro
 65                  70                  75                  80

Lys Ile Asp Arg Gly Ser Tyr Tyr Gly Lys Arg Leu Leu Leu Pro Asp
                 85                  90                  95

Ser Val Thr Glu Tyr Asp Lys Lys Leu Val Ser Arg Ile Gln Ile Arg
                100                 105                 110

Val Asn Pro Leu Pro Lys Phe Asp Ser Thr Val Trp Val Thr Val Arg
                115                 120                 125

Lys Val Pro Ala Ser Ser Asp Leu Ser Val Ala Ala Ile Ser Ala Met
    130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                    165                 170                 175

Ala Asp Ile Gly Asp Met Arg Lys Tyr Ala Val Leu Val Tyr Ser Lys
                180                 185                 190

Asp Asp Ala Leu Glu Thr Asp Glu Leu Val Leu His Val Asp Val Glu
                195                 200                 205

His Gln Arg Ile Pro Thr Ser Gly Val Leu Pro Val
    210                 215                 220

<210> SEQ ID NO 8
<211> LENGTH: 34
<212> TYPE: DNA
<213> ORGANISM: artificial sequence
<220> FEATURE:
<223> OTHER INFORMATION: primer CMcpF

<400> SEQUENCE: 8
caccatggac aaatctgaat caaccagtgc tggt                              34

<210> SEQ ID NO 9
<211> LENGTH: 37
<212> TYPE: DNA
<213> ORGANISM: artificial sequence
<220> FEATURE:
<223> OTHER INFORMATION: primer CMcpR

<400> SEQUENCE: 9
caaagcttat caaactggga gcacccgaga tgtggga                           37

<210> SEQ ID NO 10
<211> LENGTH: 660
<212> TYPE: DNA
<213> ORGANISM: cucumber mosaic virus

<400> SEQUENCE: 10
atggacaaat ctgaatcaac cagtgctggt cgtagccgtc gacgtcgtcc gcgtcgtggt    60
tcccgctccg ccccctcctc cgcggatgct aactttagag tcttgtcgca gcagctttcg   120
cgacttaata agacgttagc agctggtcgt ccaactatta accacccaac ctttgtaggg   180
agtgaacgct gtaaacctgg gtacacgttc acatctatca ccctaaagcc accaaaaata   240
gaccgtgggt cttattatgg taaaggttg ttattacctg attcagtcac ggaatatgat   300
aagaaacttg tttcgcgcat tcaaattcga gttaatcctt tgccgaaatt tgattcaacc   360
```

```
gtgtgggtga cagtccgtaa agttcctgcc tcttcggact tatccgttgc cgccatttct    420
gctatgtttg cggacggagc ctcaccggta ctggtttatc agtacgctgc atctggagtc    480
caagctaaca acaaactgtt gtatgatctt tcggcgatgc gcgctgatat aggcgacatg    540
agaaagtacg ccgtcctcgt gtattcaaaa gacgatgcac tcgagacaga cgagttagta    600
cttcatgttg acgtcgagca ccaacgtatt cccacatctg gggtgctccc agtttgataa    660
```

<210> SEQ ID NO 11
<211> LENGTH: 20
<212> TYPE: DNA
<213> ORGANISM: artificial sequence
<220> FEATURE:
<223> OTHER INFORMATION: primer pET-220

<400> SEQUENCE: 11

```
agcaccgccg ccgcaaggaa                                                 20
```

<210> SEQ ID NO 12
<211> LENGTH: 52
<212> TYPE: DNA
<213> ORGANISM: artificial sequence
<220> FEATURE:
<223> OTHER INFORMATION: primer CMV-tt83-1R

<400> SEQUENCE: 12

```
atttggagtt ggccttaata tactggccca tggtatatct ccttcttaaa gt            52
```

<210> SEQ ID NO 13
<211> LENGTH: 52
<212> TYPE: DNA
<213> ORGANISM: artificial sequence
<220> FEATURE:
<223> OTHER INFORMATION: primer CMV-tt83Sal-R2

<400> SEQUENCE: 13

```
gacgtcgacg ctcggtaatc ccgataaatt tggagttggc cttaatatac tg            52
```

<210> SEQ ID NO 14
<211> LENGTH: 672
<212> TYPE: DNA
<213> ORGANISM: artificial sequence
<220> FEATURE:
<223> OTHER INFORMATION: cDNA coding for CMV-Ntt830

<400> SEQUENCE: 14

```
atgggccagt atattaaggc caactccaaa tttatcggga ttaccgagcg tcgacgtcgt     60
ccgcgtcgtg gttcccgctc cgcccccctcc tccgcggatg ctaactttag agtcttgtcg    120
cagcagcttt cgcgacttaa taagacgtta gcagctggtc gtccaactat taaccaccca    180
acctttgtag ggagtgaacg ctgtaaacct gggtacacgt tcacatctat caccctaaag    240
ccaccaaaaa tagaccgtgg gtcttattat ggtaaaaggt tgttattacc tgattcagtc    300
acggaatatg ataagaaact tgtttcgcgc attcaaattc gagttaatcc tttgccgaaa    360
tttgattcaa ccgtgtgggt gacagtccgt aaagttcctg cctcttcgga cttatccgtt    420
gccgccattt ctgctatgtt tgcggacgga gcctcaccgg tactggttta tcagtacgct    480
gcatctggag tccaagctaa caacaaactg ttgtatgatc tttcggcgat gcgcgctgat    540
ataggcgaca tgagaaagta cgccgtcctc gtgtattcaa agacgatgc actcgagaca    600 gacgagttag tacttcatgt tgacgtcgag caccaacgta ttcccacatc tggggtgctc    660
```

```
ccagtttgat aa                                                          672
```

<210> SEQ ID NO 15
<211> LENGTH: 55
<212> TYPE: DNA
<213> ORGANISM: artificial sequence
<220> FEATURE:
<223> OTHER INFORMATION: primer CMV-padrSal-R

<400> SEQUENCE: 15

```
gacgtcgacg cgcggccgcc ttgagggtcc acgcggccac aaatttcgcc atggt           55
```

<210> SEQ ID NO 16
<211> LENGTH: 666
<212> TYPE: DNA
<213> ORGANISM: artificial sequence
<220> FEATURE:
<223> OTHER INFORMATION: cDNA coding for CMV-Npadr

<400> SEQUENCE: 16

```
atggcgaaat ttgtggccgc gtggaccctc aaggcggccg cgcgtcgacg tcgtccgcgt       60
cgtggttccc gctccgcccc ctcctccgcg gatgctaact ttagagtctt gtcgcagcag      120 cttctcgcgac ttaataagac gttagcagct ggtcgtccaa ctattaacca cccaaccttt     180
gtagggagtg aacgctgtaa acctgggtac acgttcacat ctatcaccct aaagccacca      240
aaaatagacc gtgggtctta ttatggtaaa aggttgttat tacctgattc agtcacggaa      300
tatgataaga aacttgtttc gcgcattcaa attcgagtta atcctttgcc gaaatttgat      360
tcaaccgtgt gggtgacagt ccgtaaagtt cctgcctctt cggacttatc cgttgccgcc      420
atttctgcta tgtttgcgga cggagcctca ccggtactgg tttatcagta cgctgcatct      480
ggagtccaag ctaacaacaa actgttgtat gatctttcgg cgatgcgcgc tgatataggc      540
gacatgagaa agtacgccgt cctcgtgtat tcaaaagacg atgcactcga gacagacgag      600
ttagtacttc atgttgacgt cgagcaccaa cgtattccca catctggggt gctcccagtt      660
tgataa                                                                 666
```

<210> SEQ ID NO 17
<211> LENGTH: 15
<212> TYPE: PRT
<213> ORGANISM: artificial sequence
<220> FEATURE:
<223> OTHER INFORMATION: 15 aa spacer

<400> SEQUENCE: 17

```
Gly Gly Gly Gly Ser Gly Gly Gly Gly Ser Gly Gly Gly Gly Ser
1               5                  10                  15
```

<210> SEQ ID NO 18
<211> LENGTH: 9
<212> TYPE: PRT
<213> ORGANISM: artificial sequence
<220> FEATURE:
<223> OTHER INFORMATION: HisTag plus linker

<400> SEQUENCE: 18

```
His His His His His His Gly Gly Cys
1               5
```

<210> SEQ ID NO 19
<211> LENGTH: 579
<212> TYPE: DNA
<213> ORGANISM: artificial sequence

<220> FEATURE:
<223> OTHER INFORMATION: F12H6GGC

<400> SEQUENCE: 19

```
catatggaaa tttgtccggc agttaaacgt gatgttgacc tgtttctgac cggtacaccg    60
gatgaatatg tggaacaggt tgcacagtat aaagcactgc cggttgttct ggaaaatgca   120
cgtattctga aaaattgcgt ggatgccaaa atgaccgaag aggataaaga aaatgccctg   180
agcgttctgg ataaaatcta taccagtccg ctgtgcggtg gtggtggtag tggtggcggt   240
ggttcaggcg gtggcggtag cgttaaaatg gcagaaacct gtccgatctt tatgatgtt   300
ttttttgccg tggccaatgg caatgaactg ctgctggatc tgagcctgac caaagttaat   360
gcaaccgaac cggaacgtac cgcaatgaaa aaaatccagg attgctatgt ggaaaacggt   420
ctgattagcc gtgttctgga tggtctggtt atgaccacca ttagcagcag caaagattgt   480
atgggtgaag cagtgcagaa taccgttgaa gatctgaaac tgaataccct gggtcgtcat   540
catcatcacc atcatggtgg ttgttaataa ctcgagtaa                          579
```

<210> SEQ ID NO 20
<211> LENGTH: 187
<212> TYPE: PRT
<213> ORGANISM: artificial sequence
<220> FEATURE:
<223> OTHER INFORMATION: F12H6GGC

<400> SEQUENCE: 20

```
Met Glu Ile Cys Pro Ala Val Lys Arg Asp Val Asp Leu Phe Leu Thr
1               5                   10                  15
Gly Thr Pro Asp Glu Tyr Val Glu Gln Val Ala Gln Tyr Lys Ala Leu
            20                  25                  30
Pro Val Val Leu Glu Asn Ala Arg Ile Leu Lys Asn Cys Val Asp Ala
        35                  40                  45
Lys Met Thr Glu Glu Asp Lys Glu Asn Ala Leu Ser Val Leu Asp Lys
    50                  55                  60
Ile Tyr Thr Ser Pro Leu Cys Gly Gly Gly Ser Gly Gly Gly Gly
65                  70                  75                  80
Ser Gly Gly Gly Gly Ser Val Lys Met Ala Glu Thr Cys Pro Ile Phe
                85                  90                  95
Tyr Asp Val Phe Phe Ala Val Ala Asn Gly Asn Glu Leu Leu Leu Asp
            100                 105                 110
Leu Ser Leu Thr Lys Val Asn Ala Thr Glu Pro Glu Arg Thr Ala Met
        115                 120                 125
Lys Lys Ile Gln Asp Cys Tyr Val Glu Asn Gly Leu Ile Ser Arg Val
    130                 135                 140
Leu Asp Gly Leu Val Met Thr Thr Ile Ser Ser Ser Lys Asp Cys Met
145                 150                 155                 160
Gly Glu Ala Val Gln Asn Thr Val Glu Asp Leu Lys Leu Asn Thr Leu
                165                 170                 175
Gly Arg His His His His His His Gly Gly Cys
            180                 185
```

<210> SEQ ID NO 21
<211> LENGTH: 28
<212> TYPE: DNA
<213> ORGANISM: artificial sequence
<220> FEATURE:
<223> OTHER INFORMATION: Primer Fel_BglF

<400> SEQUENCE: 21
tgaagatctg aaactgaata ccctgggt        28

<210> SEQ ID NO 22
<211> LENGTH: 49
<212> TYPE: DNA
<213> ORGANISM: artificial sequence
<220> FEATURE:
<223> OTHER INFORMATION: Reverse Primer Fe16H-cgR

<400> SEQUENCE: 22
tactcgagaa gcttattatc cacaaccacc atgatggtga tgatgatga        49

<210> SEQ ID NO 23
<211> LENGTH: 48
<212> TYPE: DNA
<213> ORGANISM: artificial sequence
<220> FEATURE:
<223> OTHER INFORMATION: Reverse Primer Feld-dHR

<400> SEQUENCE: 23
tactcgagtt attaacaacc accacgaccc agggtattca gtttcaga        48

<210> SEQ ID NO 24
<211> LENGTH: 61
<212> TYPE: DNA
<213> ORGANISM: artificial sequence
<220> FEATURE:
<223> OTHER INFORMATION: Reverse Primer Feld-dH-cgR

<400> SEQUENCE: 24
tactcgagaa gcttattatc cacaaccacc acgacccagg gtattcagtt tcagatcttc        60
a        61

<210> SEQ ID NO 25
<211> LENGTH: 188
<212> TYPE: PRT
<213> ORGANISM: artificial sequence
<220> FEATURE:
<223> OTHER INFORMATION: F12H6GGCG

<400> SEQUENCE: 25

Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
        35                  40                  45

Lys Met Thr Glu Glu Asp Lys Glu Asn Ala Leu Ser Val Leu Asp Lys
    50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
                85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
        115                 120                 125

Lys Lys Ile Gln Asp Cys Tyr Val Glu Asn Gly Leu Ile Ser Arg Val
    130                 135                 140

```
Leu Asp Gly Leu Val Met Thr Thr Ile Ser Ser Ser Lys Asp Cys Met
145                 150                 155                 160

Gly Glu Ala Val Gln Asn Thr Val Glu Asp Leu Lys Leu Asn Thr Leu
                165                 170                 175

Gly Arg His His His His His His Gly Gly Cys Gly
            180                 185
```

<210> SEQ ID NO 26
<211> LENGTH: 181
<212> TYPE: PRT
<213> ORGANISM: artificial sequence
<220> FEATURE:
<223> OTHER INFORMATION: F12GGC

<400> SEQUENCE: 26

```
Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
                20                  25                  30

Pro Val Val Leu Glu Asn Ala Arg Ile Leu Lys Asn Cys Val Asp Ala
            35                  40                  45

Lys Met Thr Glu Glu Asp Lys Glu Asn Ala Leu Ser Val Leu Asp Lys
50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
                85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
            115                 120                 125

Lys Lys Ile Gln Asp Cys Tyr Val Glu Asn Gly Leu Ile Ser Arg Val
130                 135                 140

Leu Asp Gly Leu Val Met Thr Thr Ile Ser Ser Ser Lys Asp Cys Met
145                 150                 155                 160

Gly Glu Ala Val Gln Asn Thr Val Glu Asp Leu Lys Leu Asn Thr Leu
                165                 170                 175

Gly Arg Gly Gly Cys
            180
```

<210> SEQ ID NO 27
<211> LENGTH: 182
<212> TYPE: PRT
<213> ORGANISM: artificial sequence
<220> FEATURE:
<223> OTHER INFORMATION: F12GGCG

<400> SEQUENCE: 27

```
Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
                20                  25                  30

Pro Val Val Leu Glu Asn Ala Arg Ile Leu Lys Asn Cys Val Asp Ala
            35                  40                  45

Lys Met Thr Glu Glu Asp Lys Glu Asn Ala Leu Ser Val Leu Asp Lys
50                  55                  60

Ile Tyr Thr Ser Pro Leu Cys Gly Gly Gly Ser Gly Gly Gly Gly
65                  70                  75                  80
```

```
Ser Gly Gly Gly Gly Ser Val Lys Met Ala Glu Thr Cys Pro Ile Phe
            85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
            115                 120                 125

Lys Lys Ile Gln Asp Cys Tyr Val Glu Asn Gly Leu Ile Ser Arg Val
            130                 135                 140

Leu Asp Gly Leu Val Met Thr Thr Ile Ser Ser Lys Asp Cys Met
145                 150                 155                 160

Gly Glu Ala Val Gln Asn Thr Val Glu Asp Leu Lys Leu Asn Thr Leu
            165                 170                 175

Gly Arg Gly Gly Cys Gly
            180

<210> SEQ ID NO 28
<211> LENGTH: 4
<212> TYPE: PRT
<213> ORGANISM: artificial sequence
<220> FEATURE:
<223> OTHER INFORMATION: linker sequence

<400> SEQUENCE: 28

Gly Gly Cys Gly
1

<210> SEQ ID NO 29
<211> LENGTH: 178
<212> TYPE: PRT
<213> ORGANISM: artificial sequence
<220> FEATURE:
<223> OTHER INFORMATION: F12

<400> SEQUENCE: 29

Met Glu Ile Cys Pro Ala Val Lys Arg Asp Val Asp Leu Phe Leu Thr
1               5                   10                  15

Gly Thr Pro Asp Glu Tyr Val Glu Gln Val Ala Gln Tyr Lys Ala Leu
            20                  25                  30

Pro Val Val Leu Glu Asn Ala Arg Ile Leu Lys Asn Cys Val Asp Ala
            35                  40                  45

Lys Met Thr Glu Glu Asp Lys Glu Asn Ala Leu Ser Val Leu Asp Lys
        50                  55                  60

Ile Tyr Thr Ser Pro Leu Cys Gly Gly Gly Ser Gly Gly Gly Gly
65                  70                  75                  80

Ser Gly Gly Gly Gly Ser Val Lys Met Ala Glu Thr Cys Pro Ile Phe
            85                  90                  95

Tyr Asp Val Phe Phe Ala Val Ala Asn Gly Asn Glu Leu Leu Leu Asp
            100                 105                 110

Leu Ser Leu Thr Lys Val Asn Ala Thr Glu Pro Glu Arg Thr Ala Met
            115                 120                 125

Lys Lys Ile Gln Asp Cys Tyr Val Glu Asn Gly Leu Ile Ser Arg Val
            130                 135                 140

Leu Asp Gly Leu Val Met Thr Thr Ile Ser Ser Lys Asp Cys Met
145                 150                 155                 160

Gly Glu Ala Val Gln Asn Thr Val Glu Asp Leu Lys Leu Asn Thr Leu
            165                 170                 175

Gly Arg
```

<210> SEQ ID NO 30
<211> LENGTH: 70
<212> TYPE: PRT
<213> ORGANISM: Felis domesticus

<400> SEQUENCE: 30

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
    50                  55                  60

Tyr Thr Ser Pro Leu Cys
65                  70

<210> SEQ ID NO 31
<211> LENGTH: 92
<212> TYPE: PRT
<213> ORGANISM: Felis domesticus

<400> SEQUENCE: 31

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Thr Thr Ile Ser Ser Ser Lys Asp Cys Met Gly Glu Ala Val Gln Asn
65                  70                  75                  80

Thr Val Glu Asp Leu Lys Leu Asn Thr Leu Gly Arg
                85                  90

<210> SEQ ID NO 32
<211> LENGTH: 90
<212> TYPE: PRT
<213> ORGANISM: Felis domesticus

<400> SEQUENCE: 32

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
            20                  25                  30

Asn Ala Thr Glu Pro Glu Arg Thr Ala Met Lys Lys Ile Gln Asp Cys
        35                  40                  45

Tyr Val Glu Asn Gly Leu Ile Ser Arg Val Leu Asp Gly Leu Val Met
    50                  55                  60

Ile Ala Ile Asn Glu Tyr Cys Met Gly Glu Ala Val Gln Asn Thr Val
65                  70                  75                  80

Glu Asp Leu Lys Leu Asn Thr Leu Gly Arg
                85                  90

<210> SEQ ID NO 33
<211> LENGTH: 78

```
<212> TYPE: PRT
<213> ORGANISM: Felis domesticus

<400> SEQUENCE: 33

Val Lys Met Ala Glu Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
                20                  25                  30

Asn Ala Thr Glu Pro Glu Arg Thr Ala Met Lys Lys Ile Gln Asp Cys
            35                  40                  45

Tyr Val Glu Asn Gly Leu Ile Ser Arg Val Leu Asp Gly Leu Val Met
        50                  55                  60

Pro Ser Thr Asn Ile Ala Trp Val Lys Gln Phe Arg Thr Pro
65                  70                  75

<210> SEQ ID NO 34
<211> LENGTH: 27
<212> TYPE: PRT
<213> ORGANISM: artificial sequence
<220> FEATURE:
<223> OTHER INFORMATION: aa 2-28 of SEQ ID NO:1

<400> SEQUENCE: 34

Asp Lys Ser Glu Ser Thr Ser Ala Gly Arg Ser Arg Arg Arg Arg Pro
1               5                   10                  15

Arg Arg Gly Ser Arg Ser Ala Pro Ser Ser Ala
                20                  25
```

COMPOSITIONS AGAINST CAT ALLERGY

The present invention relates to the use of a composition in a method of reducing the allergenicity of a cat for a human. Moreover, the present invention relates to the use of a composition in a method of reducing the allergenicity of a cat for a human exposed to the cat. Furthermore, the present invention relates to compositions comprising a virus-like particle (VLP) and at least one Fel d1 protein. The compositions of the invention induce efficient immune responses, in particular antibody responses, in cats reducing the allergenicity of the Fel d1 shed by the cats and are, therefore, useful for the treatment and/or prevention of cat allergy in humans.

RELATED ART

The domestic cat (*Felis domesticus*) is an important source of indoor allergens (Lau, S., et al. (2000) Lancet 356, 1392-1397). Indeed, cats are found in about 25% of households in Western countries and allergy to cats is found in a large part of the population. The severity of symptoms range from relatively mild rhinitis and conjunctivitis to potentially life-threatening asthmatic exacerbation. Although patients are occasionally sensitized to several different molecules in cat dander and pelts, the major allergen is Fel d1. The importance of this allergen has been emphasized in numerous studies. In fact more than 80% of cat allergic patients exhibit IgE antibodies to this potent allergen (van Ree, R., et al. (1999) J. Allergy Clin Immunol 104, 1223-1230).

Fel d1 is a 35-39 kDa acidic glycoprotein containing 10-20% N-linked carbohydrates and is found in the pelt, i.e. the skin and the fur, in the salivary and lacrimal glands as well as in perianal glands of cats. It is formed by two non-covalently linked heterodimers. Each heterodimer consists of one 70 residue peptide (known as "chain 1") and one 78, 85, 90 or 92 residue peptide (known as "chain 2") which are encoded by separate genes (see Duffort, O. A., et al. (1991) Mol Immunol 28, 301-309; Morgenstern, J. P., et al; (1991) Proc Natl Acad Sci USA 88, 9690-9694 and Griffith, I. J., et al. (1992) Gene 113, 263-268).

Treatment of cat allergic patients is currently effected by desensitization therapy involving repeated injections with increasing dosages of either a crude cat dander extract or short peptides derived from Fel d1. Lilja et al and Hedlin et al have disclosed a desensitization program in the course of which crude cat dander extracts have been given to cat allergic patients (Lilja, Q, et al. (1989) J Allergy Clin Immunol 83, 37-44 and Hedlin, et al. (1991) J Allergy Clin Immunol 87, 955-964). This program took at least two to three years and the patients after three year treatment still had systemic symptoms. Using short peptides derived from Fel d1 for desensitization resulted in non-significant difference between the peptide group and the placebo group (Oldfield, W. L., et al. (2002) Lancet 360, 47-53). Efficacy was only seen when large amount (750 μg) of the short peptide was given to patients (Norman, P. S., et al. (1996) Am J Respir Crit Care Med 154, 1623-1628).

Allergic side effects, such as late asthmatic reactions, have been reported in both crude cat dander extract treatment and in short peptide treatment. Therefore, anaphylactic shock due to the injected allergen is of great safety concern for any desensitization program. Avoidance of such effect by reducing the injected amount of allergen, however, either reduces the efficacy of the treatment or prolongs the treatment. Thus, there is a great need in the field of cat-allergy treatment for alternative desensitization regimes, and hereby in particular for desensitization regimes that are able to reduce allergic symptoms, but do not trigger allergic side reaction. Active immunization in humans with Fel d1 antigens covalently linked to virus-like particles has also been described to address cat allergy in humans (WO2006/097530A2).

Alternatively, treating the cat itself has been suggested to reduce the amount of Fel d1 shed by a cat (WO2007/113633A2). However, no data, let alone reports of success, have ever since been provided.

As a consequence, there is a need for compositions and treatments shown to be effective in addressing cat allergy in humans. In particular, there is a need for compositions and treatments shown to be effective in a method of reducing the allergenicity of a cat for a human.

SUMMARY OF THE INVENTION

We have shown that compositions of the present invention are effective in a method of reducing the allergenicity of a cat, and hereby in particular the allergenicity of a cat for a human. Thus, we have found that administration of the compositions of the present invention to a cat led to the generation of Fel d1-specific IgG antibodies as well as of Fel d1-specific IgA antibodies. Moreover, immune complexes consisting of endogenous Fel d1 and IgA antibodies were detected in the immunized cats. Furthermore, saliva extracts from cats taken after immunization with the said compositions showed decreased levels of degranulation of basophils from cat allergic patients by up to 20% when compared to saliva extracts taken from said cats before immunization which corresponds to a 13-fold decrease in Fel d1 concentration and indicating that a significant reduction in allergenic Fel d1 in saliva was achieved.

Without being bound by this explanation, the present invention impacts the allergic response in humans at the first possible point of intervention by inducing Fel d1-specific IgG and IgA antibodies in cats, which will bind Fel d1 and thus lower or neutralize the allergenic effect of Fel d1. Upon administration of an effective amount of the compositions of the present invention, a humoral immune response against Fel d1 as well against the VLP carrier is induced in the cat. The antibody response is expected to be predominantly of the IgG isotype but also IgA will be induced. These anti-Fel d1 antibodies eventually mediate protection from the allergic reaction. Following immunization and induction of Fel d1-specific antibodies, immune complexes, i.e. antibody-Fel d1 complexes, will form in situ and be secreted into the environment. Consequently humans will be exposed to complexed Fel d1 and less of the natural unbound ("reactive") form shed by the cat. This is likely to be effective via two mechanisms of action. First by reducing the engagement of Fel d1 by IgE/FcεRI (classical neutralization) and second through co-engagement of IgE/FcεRI and IgG/FcγRIIb which can de-activate FcεRI mediated signaling (negative signaling).

Thus, in a first aspect, the present invention provides for use of a composition in a method of reducing the allergenicity of a cat typically and preferably for a human, wherein an effective amount of said composition is administered to said cat, and wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site. Preferably, said method is a non-therapeutic method of reducing the allergenicity of said cat. In a further embodiment, said cat is not suffering from an allergy or an auto-immune disease, typically and preferably wherein said cat is not suffering from an allergy or an auto-immune disease caused by Fel d1.

In a preferred embodiment, said reducing the allergenicity of said cat, typically and preferably for a human, is effected by generating immune complexes formed of Fel d1 and Fel d1-antibodies in the saliva, the fur, the skin or the tears of said cat, preferably in the saliva of said cat, and wherein preferably said administration of said composition leads to said generating of said immune complexes in the saliva, fur, skin or tears of said cat, preferably in the saliva of said cat.

In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. In a further very preferred embodiment, said CMV polypeptide comprises, or preferably consists of, (a) an amino acid sequence of a coat protein of CMV, wherein said amino acid sequence comprises, or preferably consists of, SEQ ID NO: 1 or (b) an amino acid sequence having a sequence identity of at least 90% of SEQ ID NO:1; and wherein said amino sequence as defined in (a) or (b) in this claim comprises SEQ ID NO:34; or wherein said amino sequence as defined in (a) or (b) in this claim comprises an amino acid sequence region, wherein said amino acid sequence region has a sequence identity of at least 90% with SEQ ID NO:34.

In a further very preferred embodiment, said modified CMV polypeptide comprises, preferably consists of, an amino acid sequence of SEQ ID NO:6 or SEQ ID NO:7. Furthermore, very preferably said Fel d1 protein is a Fel d1 fusion protein comprising chain 1 of Fel d1 and chain 2 of Fel d1, wherein chain 1 of Fel d1 and chain 2 of Fel d1 are fused either directly via one peptide bond or via a spacer, which links the N-terminus of one chain with the C-terminus of another chain. Very preferably, said Fel d1 protein comprises an amino acid sequence selected from: (a) SEQ ID NO:20; (b) SEQ ID NO:25; (c) SEQ ID NO:26; (d) SEQ ID NO:27; or (e) SEQ ID NO:29.

In another aspect, the present invention provides for a method for reducing the allergenicity of a cat typically and preferably for a human, wherein said method comprises administering an effective amount of said composition to said cat, wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site. Preferably, said method is a non-therapeutic method of reducing the allergenicity of said cat.

In a further aspect, the present invention provides for a composition comprising (i) a virus-like particle (VLP) with at least one first attachment site; (ii) at least one Fel d1 protein with at least one second attachment site; and wherein said virus-like particle and said Fel d1 protein are linked through said at least one first and said at least one second attachment site, and wherein said Fel d1 protein comprises an amino acid sequence selected from SEQ ID NO:25 or SEQ ID NO:27; and wherein said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7.

In a further aspect, the present invention provides an immunogenic composition formulated as a composition for administration to the cat that reduces the allergenicity of the Fel d1 shed by the cat. The composition of the invention renders the cat less allergenic towards humans prone to show symptoms of cat allergy when in contact with or proximity to the cat.

In another aspect, the present invention provides for use of a composition in a method of reducing the allergenicity of a cat, wherein an effective amount of said composition is administered to said cat, and wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site, and wherein said reduced allergenicity of said cat is a reduced allergenicity of said cat for a human.

In another aspect, the present invention provides for a composition for use in a method of reducing the allergenicity of a cat, wherein an effective amount of said composition is administered to said cat, and wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site, and wherein said reduced allergenicity of said cat is a reduced allergenicity of said cat for a human Further aspects and embodiments of the present invention will be become apparent as this description continues.

BRIEF DESCRIPTION OF FIGURES

FIG. 1 pET-CMVwt plasmid map. The relative positions of relevant genes and restriction enzyme sites are denoted.

FIG. 2A Dynamic light scattering of purified CMVwt VLPs. The size of particles was detected by using Zetasizer Nano ZS (Malvern Instruments Ltd., United Kingdom).

FIG. 2B Electron-microscopy analysis of purified CMVwt VLPs. For the morphological analysis of VLPs the JEM-1230 electron microscope (Jeol Ltd., Tokyo, Japan) was used.

FIG. 3 Mass spectrometric analysis of purified CMV-derived VLPs. Matrix-assisted laser desorption/ionization (MALDI)-TOF MS analysis was carried out on an Autoflex MS (Bruker Daltonik, Germany). The protein molecular mass (MM) calibration standard II (22.3-66.5 kDa; Bruker Daltonik) was used for mass determination.

FIG. 3A CMVwild-type ("wt"); theoretical MM=24069; found MM=24058

FIG. 3B CMV-Npadr; theoretical MM=24161 (without first Met); found MM=24160

FIG. 3C CMV-Ntt830; theoretical MM=24483 (without first Met); found MM=24477

Figure 4A:
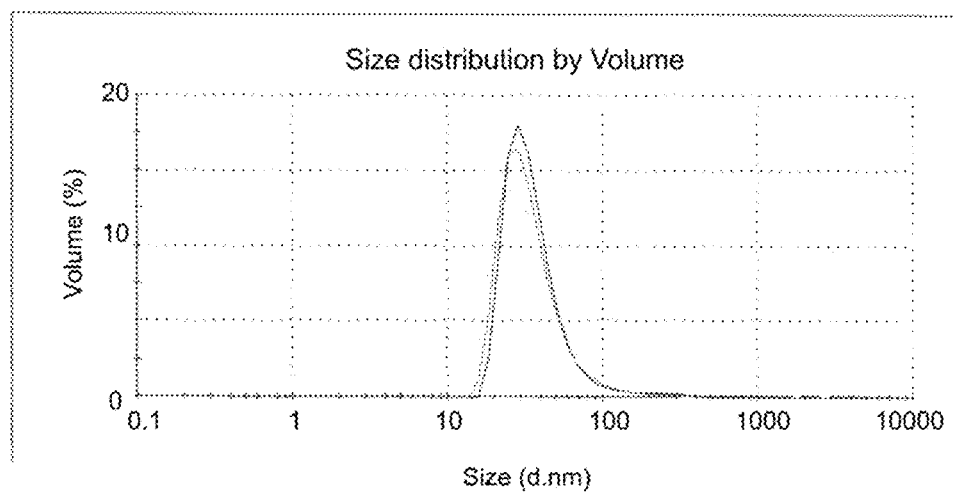

FIG. 4A Dynamic light scattering of purified CMV-Ntt830 VLPs. The size of particles was detected by using Zetasizer Nano ZS (Malvern Instruments Ltd., United Kingdom).

Figure 4B:
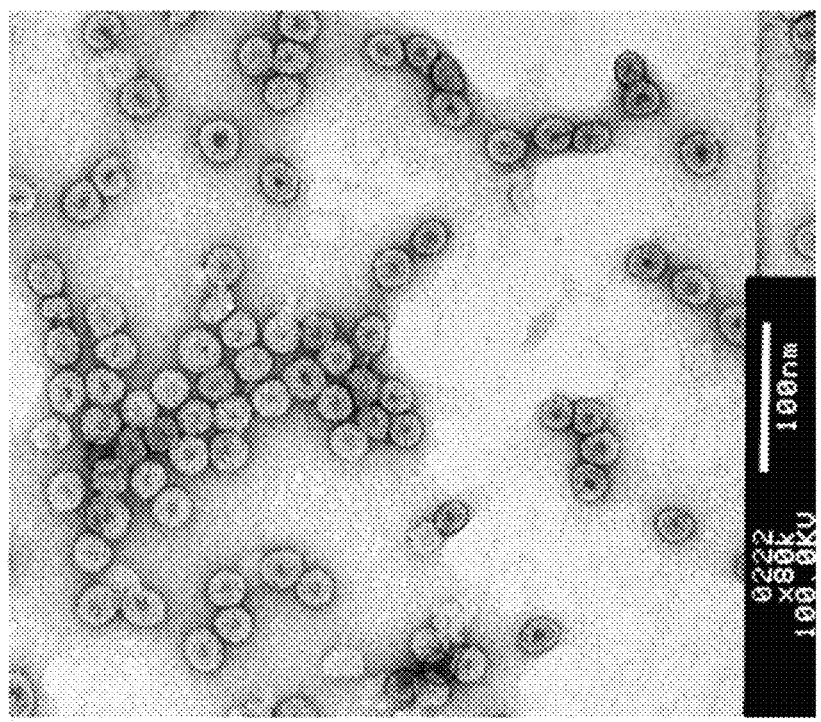

FIG. 4B Electron-microscopy analysis of purified CMV-Ntt830 VLPs. For the morphological analysis of VLPs the JEM-1230 electron microscope (Jeol Ltd., Tokyo, Japan) was used.

Figure 5A:
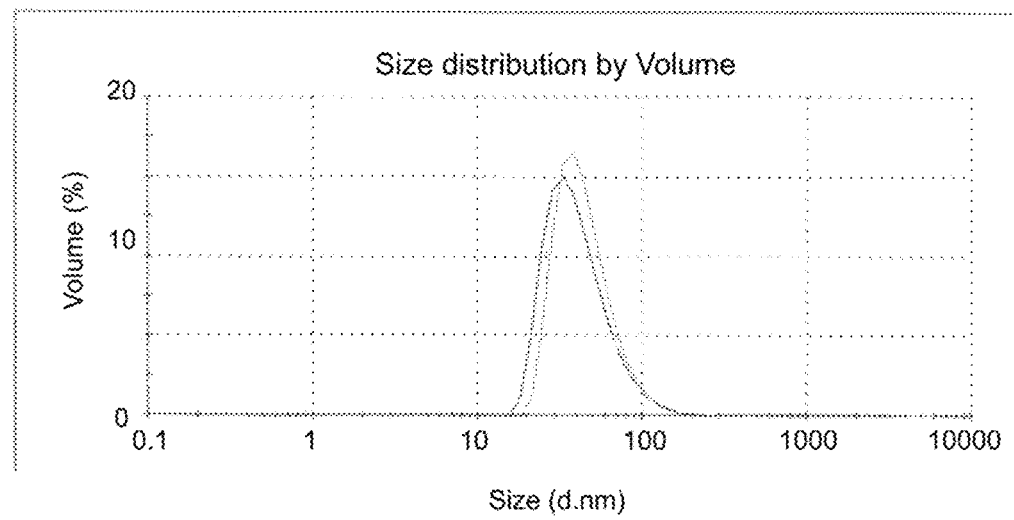

FIG. 5A Dynamic light scattering of purified CMV-Npadr VLPs. The size of particles was detected by using Zetasizer Nano ZS (Malvern Instruments Ltd., United Kingdom).

Figure 5B:
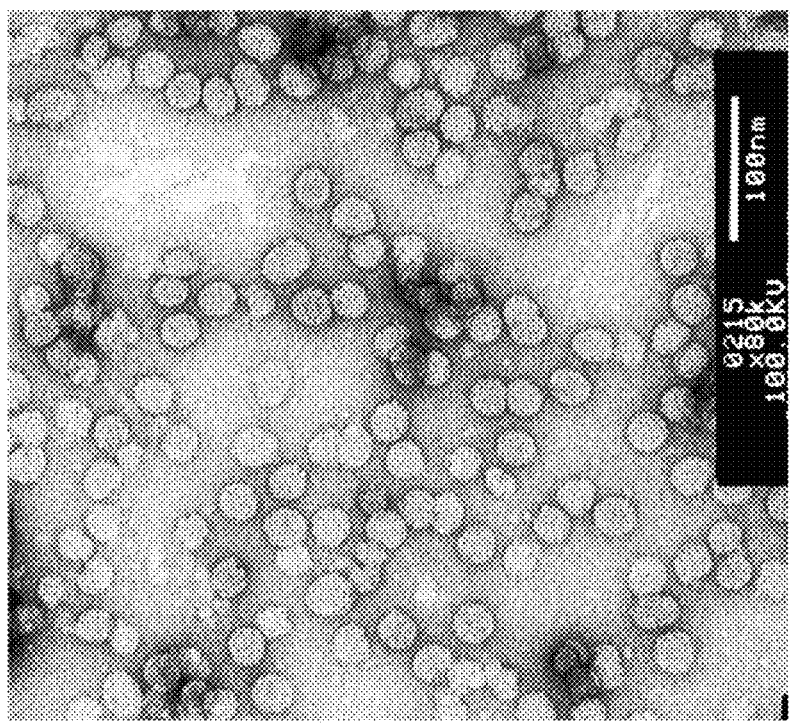

FIG. 5B Electron-microscopy analysis of purified CMV-Npadr VLPs. For the morphological analysis of VLPs the JEM-1230 electron microscope (Jeol Ltd., Tokyo, Japan) was used.

Figure 6A:
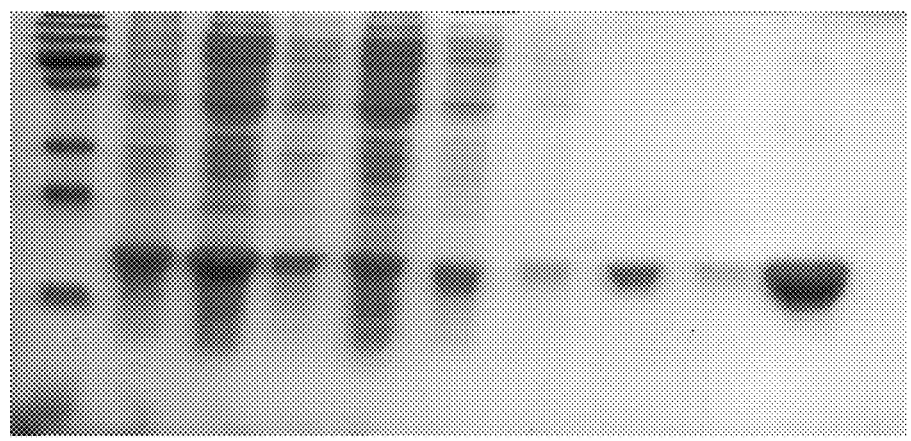

FIG. 6A SDS/PAGE analysis of expression and purification of F12H6GGC protein from E. coli C2566 cells, using PrepEase kit (USB). M—protein size marker; S—soluble protein fraction; P—cell debris; F—Flow through from Ni-IDA column (unbound proteins); W1, W2—Wash fractions (2×2 ml 1×LEW buffer) W3, W4 Wash fractions (2×2 ml 1×LEW+10 mM imidazole); E1, E2—Elution fractions (2×1.5 ml E buffer 250 mM imidazole).

Figure 6B:
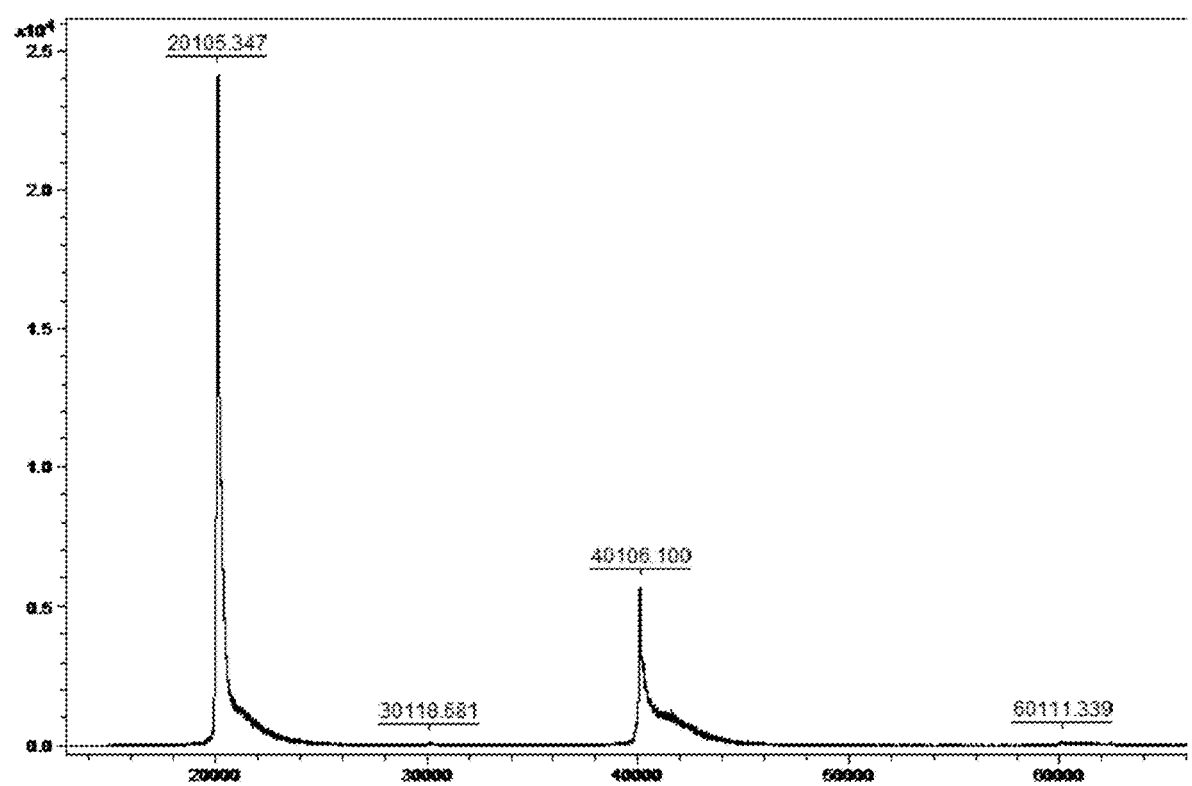

FIG. 6B Mass spectrometric analysis of purified F12H6GGC. The calculated average mass of the F12H6GGC corresponds to 20089.8 Da. The observed mass of 20105.3 corresponds to F12H6GGC with one Met sulfoxide.

Figure 6C:
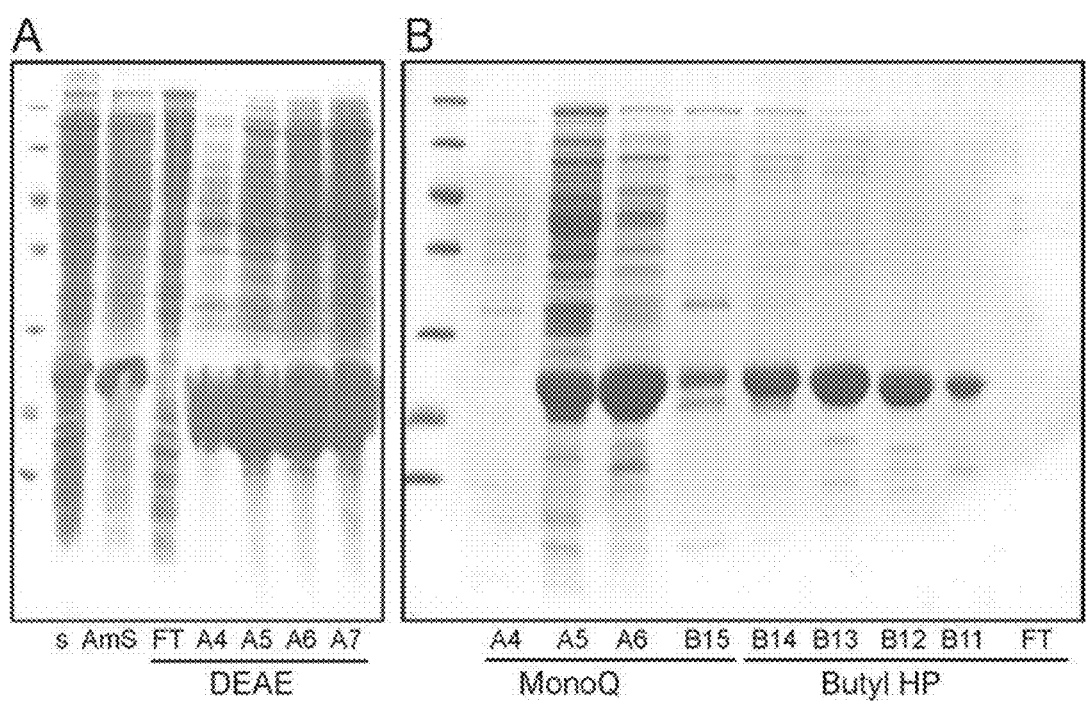

FIG. 6C Coomassie Blue stained SDS-PAGE analysis of purification of FG12GGCG. (A) s—post sonication supernatant; AmS—dissolved precipitate after 50% $(NH_4)_2SO_4$. Various fractions from the DEAE column procedure: FT—flow through, A4-A7—fractions eluted by increasing NaCl gradient (B) Subsequent purification by MonoQ and Butyl HP columns.

Figure 7:
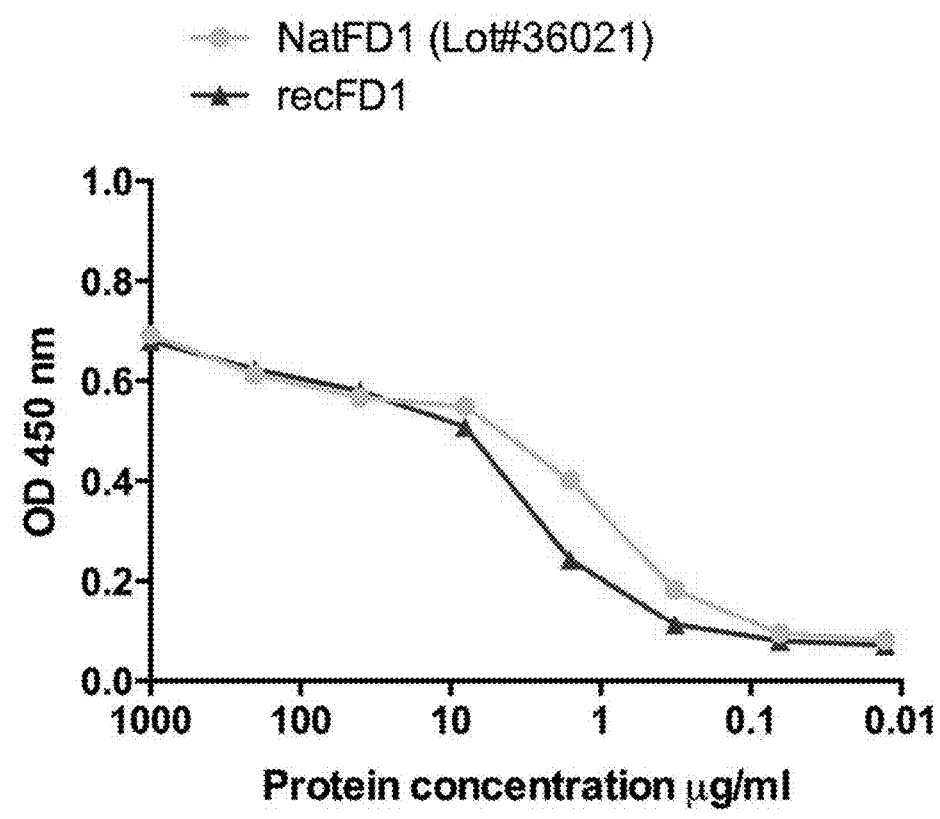

FIG. 7 A sandwich ELISA supplied from Indoor Biotechnologies using mAbs raised against the natural Fel d1 is shown. The mAbs recognize F12H6GGC and natural Fel d1 equally well.

Figure 8A:
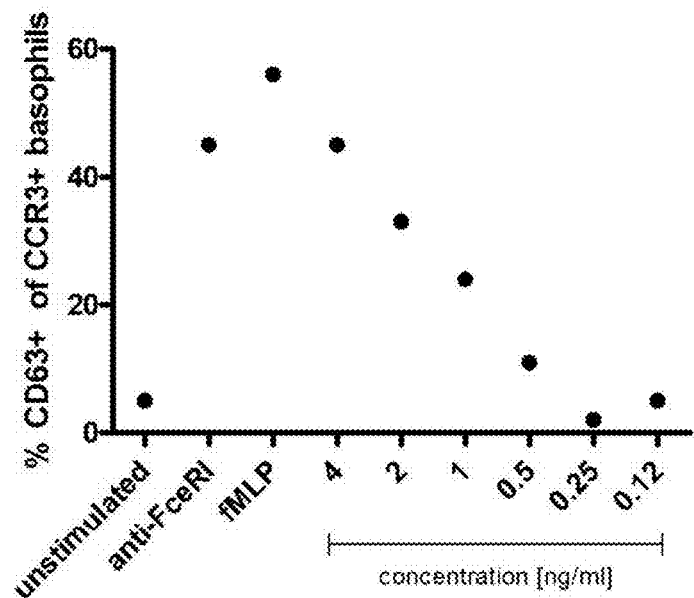

FIG. 8A Basophil activation test (BAT) for natural Fel d1.

Figure 8B:
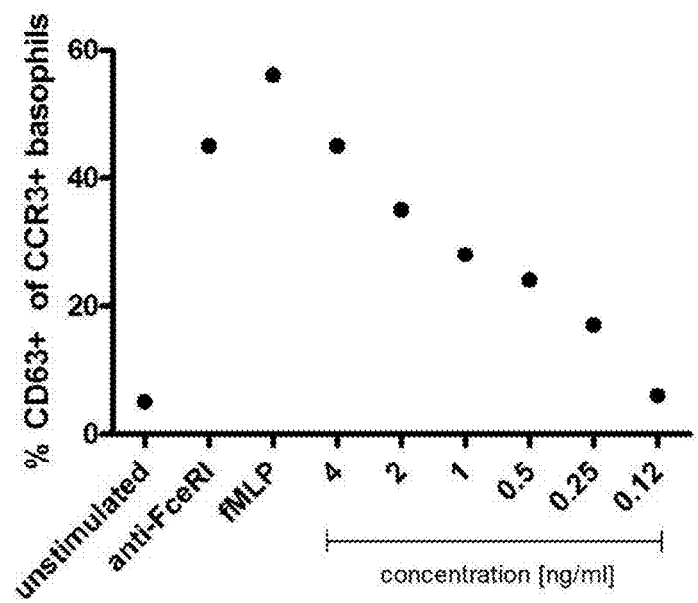

FIG. 8B Basophil activation test (BAT) for F12H6GGC. F12H6GGC and natural Fel d1 induce similar activation levels of basophils in blood from cat allergic patients indicated by the up-regulation of CD63 on CCR3+ basophils.

Figure 9:
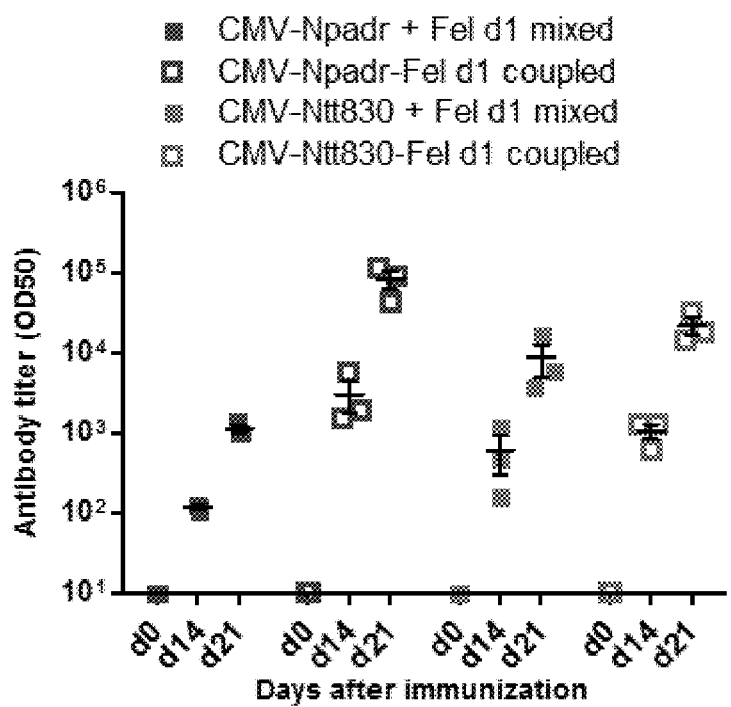

FIG. 9 Antibody response of mice which received 10 µg of either Fel d1-CMV VLPs (Fel d1-CMV-Ntt830-VLP or Fel d1-CMV-Npadr-VLP) or CMV-VLPs (CMV-Ntt830-VLP or CMV-Npadr-VLP) simply mixed with Fel d1 fusion protein F12H6GGC on day 0 and day 14. Serum was collected on day 0, 14 and 21 and analyzed by ELISA for natural Fel d1 specific IgG-antibodies. N=3.

Figure 10A:
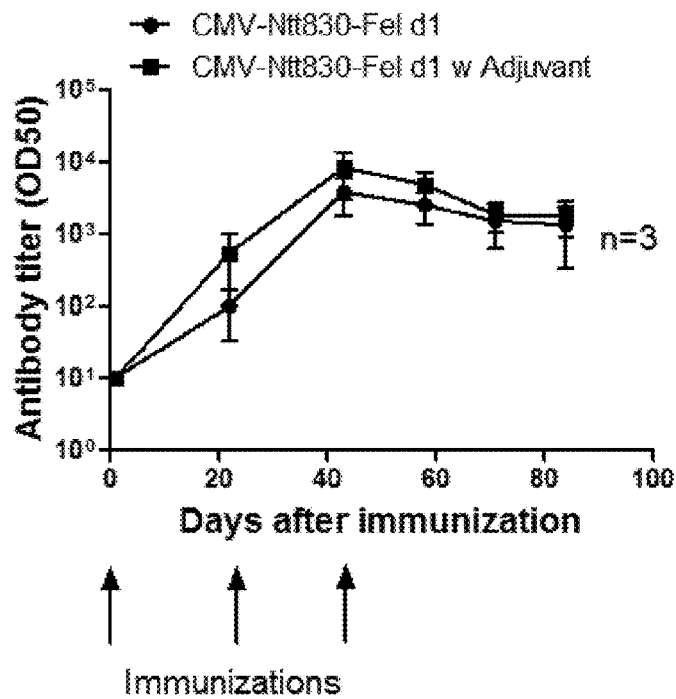
Figure 10B:
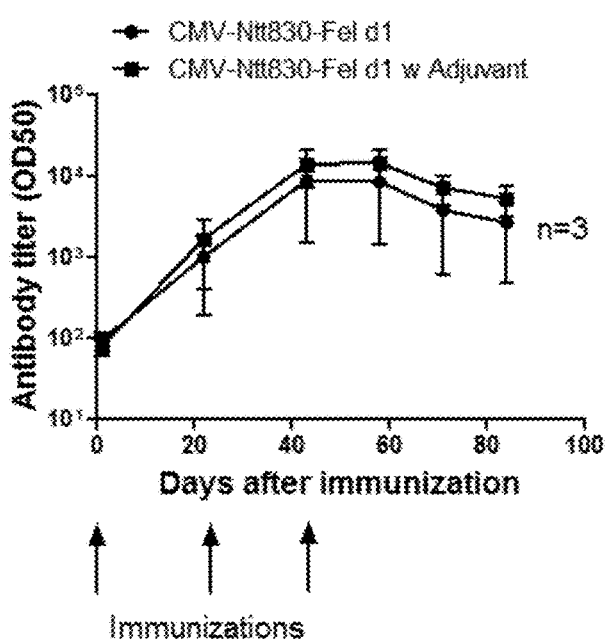
Figure 11A:
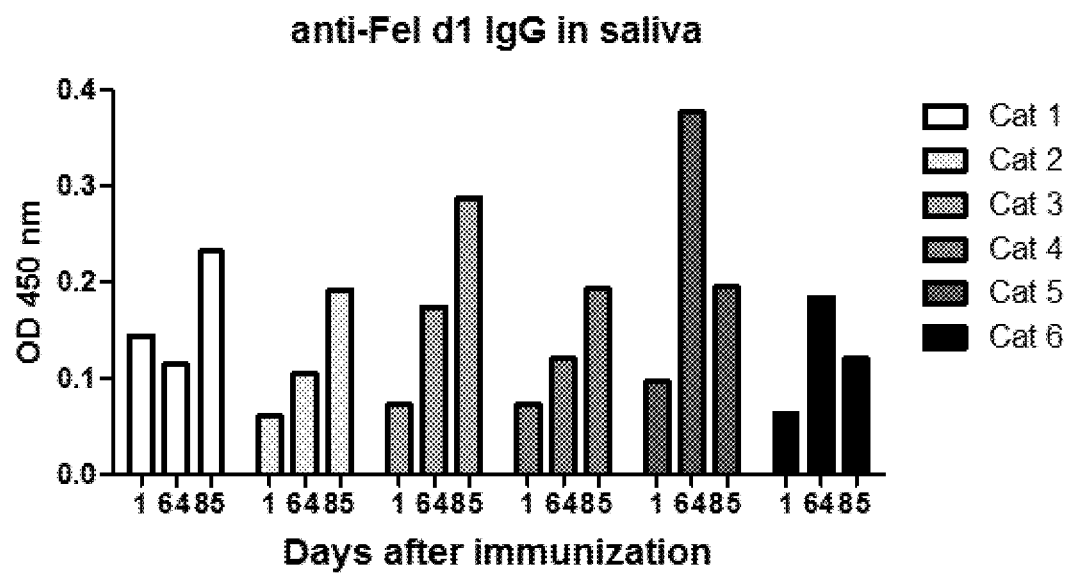
Figure 11B:
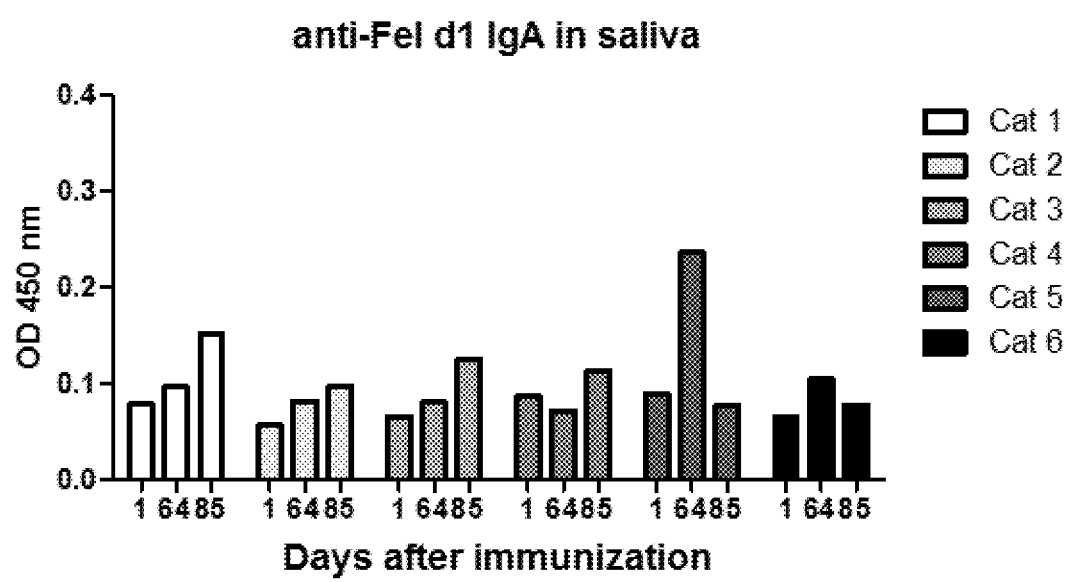
Figure 11C:
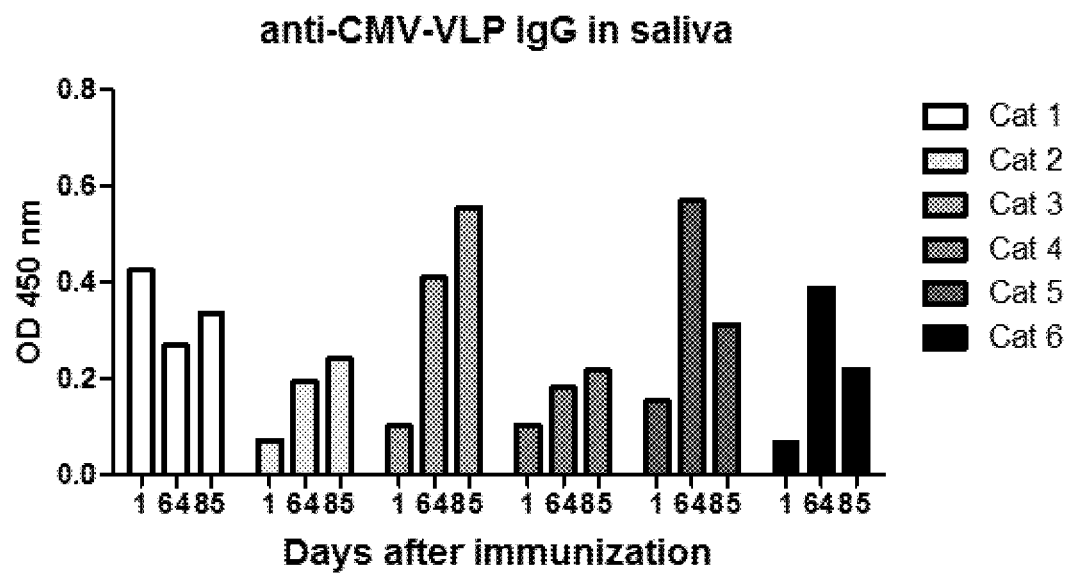
Figure 11D:
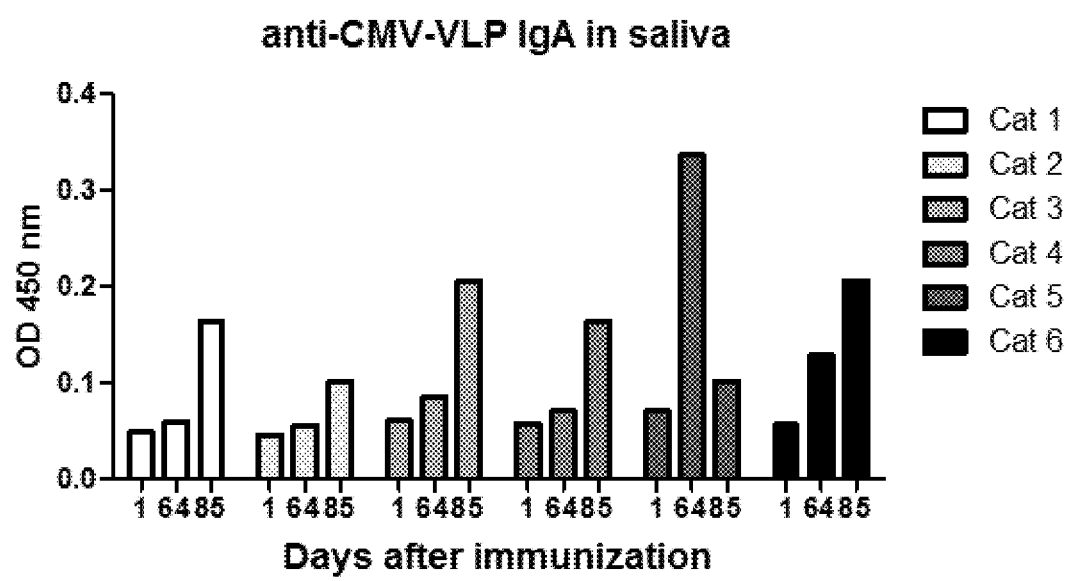

FIG. 10 IgG-antibody titer against Fel d1 and CMV in cats immunized with Fel d1-CMV-Ntt830-VLP with or without adjuvant. ELISAs were used to detect Fel d1- (FIG. 10A) and CMV- (FIG. 10B) specific IgG antibodies in sera from immunized cats.

FIG. 11 Measurement of anti-Fel d1 and anti-CMV antibodies in saliva extracts of cats. ELISAs were used to detect Fel d1-specific IgG antibodies (FIG. 11A), Fel d1-specific IgA antibodies (FIG. 11B), CMV-specific IgG antibodies (FIG. 11C) and CMV-specific IgA antibodies (FIG. 11D).

Figure 12:
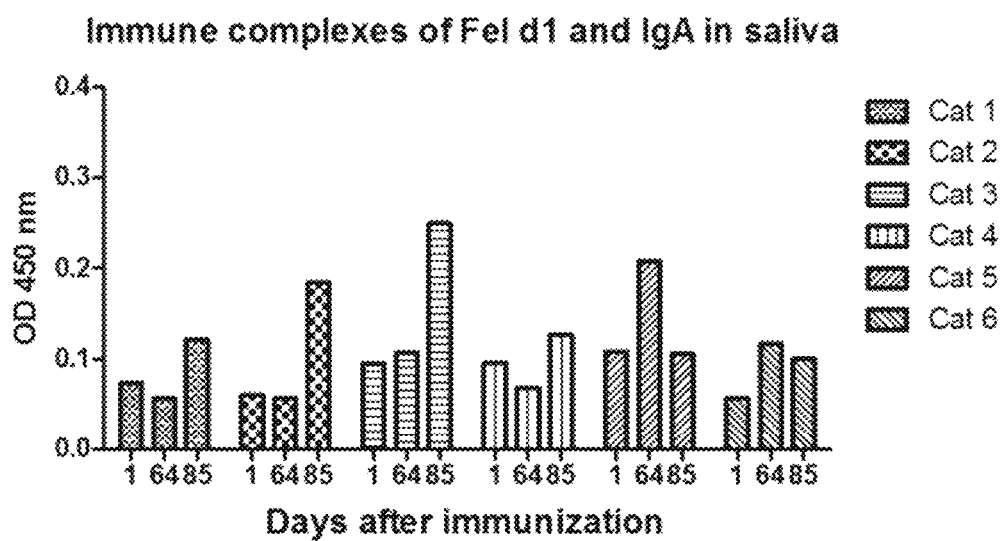

FIG. 12 Detection of immune complexes consisting of endogenous Fel d1 and IgA antibodies in saliva of immunized cats.

Figure 13A:
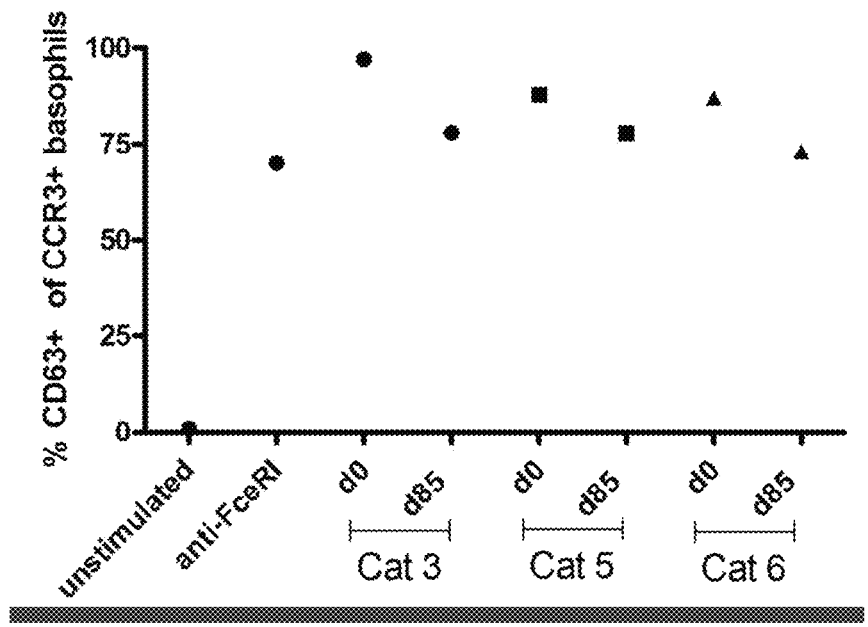
Figure 13B:
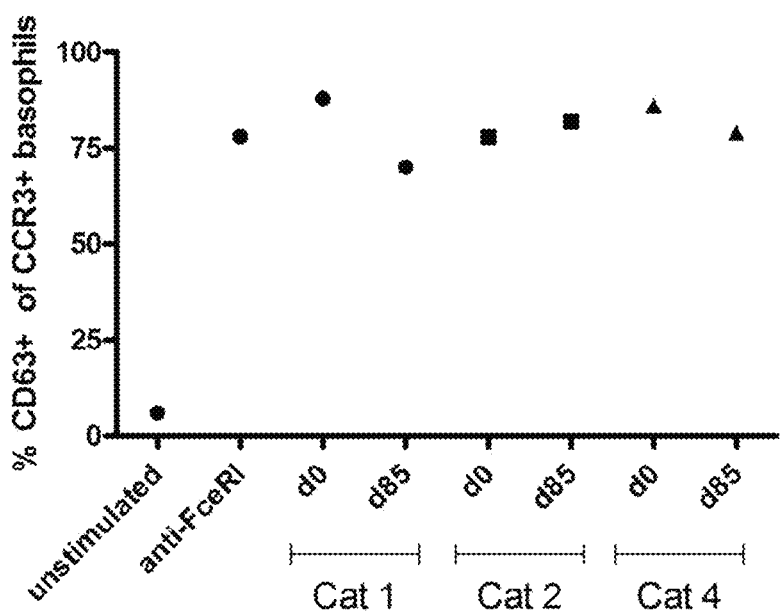

FIG. 13 Basophil activation test (BAT) with saliva samples from day 0 and day 85 show immunization with Fel d1-CMV-Ntt830-VLP reduces degranulation in 5 of 6 cats (FIG. 13A and FIG. 13B).

Figure 14:
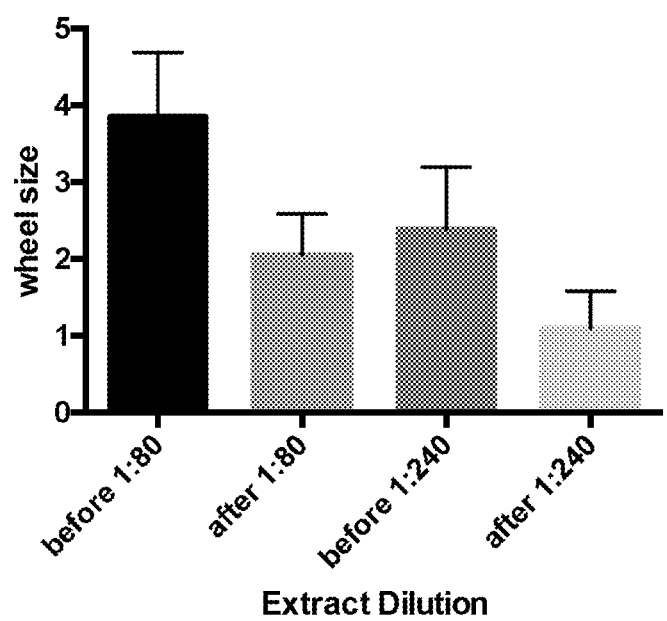

FIG. 14 Comparison of wheal size (area, mm2) from skin prick tests using cat fur extract obtained before and after immunization with Fel d1-CMV-Ntt830-VLP. Data, mean+/−standard error of the mean, are shown for cat fur extracts diluted 1:80 and 1:243 (1:240). A total of 16 skin prick tests comparing wheal size with pre and post-immunization fur extracts were successfully performed and analyzed.

DETAILED DESCRIPTION OF THE INVENTION

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, dpvweb.net or ncbi.nlm.nih.gov/protein/. Examples are described in EP Application No. 14189897.3. Further examples of CMV coat proteins are provided in SEQ ID NOs 1-3. It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in *E. coli*.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange.

Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (blast.ncbi.nlm.nih.gov/Blast.cgi) or the "CLUSTALW" (www.genome.ip/tools/clustalw/), and hereby preferably by the "BLAST" program provided on the NCBI homepage at blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Amino acid exchange: The term amino acid exchange refers to the exchange of a given amino acid residue in an amino acid sequence by any other amino acid residue having a different chemical structure, preferably by another proteinogenic amino acid residue. Thus, in contrast to insertion or deletion of an amino acid, the amino acid exchange does not change the total number of amino acids of said amino acid sequence. Very preferred in the context of the invention is the exchange of an amino acid residue of said amino acid sequence to be mutated by a lysine residue or by a cysteine residue.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell. In another preferred embodiment, said T helper cell epitope is a universal T helper cell epitope.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least $10^{-5}$M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

Effective amount: As used herein, the term "effective amount" refers to an amount necessary or sufficient to realize a desired biologic effect. An effective amount of the composition, or alternatively the pharmaceutical composition, would be the amount that achieves this selected result, and such an amount could be determined as a matter of routine by a person skilled in the art. Preferably, the term "effective amount", as used herein, refers to an amount necessary or sufficient to be effective to reduce the allergenicity of a cat typically and preferably for a human. Preferably, the term "effective amount", as used herein, refers to an amount necessary or sufficient to be effective to generate immune complexes formed of Fel d1 and Fel d1-antibodies in the saliva, the fur, the skin or the tears of a cat, preferably in the saliva of a cat as described herein. The effective amount can vary depending on the particular composition being administered and the size of the subject. One of ordinary skill in the art can empirically determine the effective amount of a particular composition of the present invention without necessitating undue experimentation.

Treatment: As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment.

Fel d1 protein: The term "Fel d1 protein", as used herein, refers to a protein comprising or alternatively consisting of chain 1 of Fel d1 and chain 2 of Fel d1. Preferably chain 1 of Fel d1 and chain 2 of Fel d1 are linked covalently. In one preferred embodiment, the chain 1 of Fel d1 and chain 2 of Fel d1 are linked via at least one disulfide bond. In another preferred embodiment, the chain 1 and chain 2 are fused either directly or via a spacer, in which case said Fel d1 protein further comprises or alternatively consists of a spacer. Preferably the Fel d1 protein, as defined herein, consists of at most 300, even more preferably at most 200 amino acids in total. Typically and preferably, Fel d1 protein, according to the invention, is capable of inducing in vivo the production of antibody specifically binding to either the naturally occurring Fel d1, the endogenous Fel d1 or the recombinant Fel d1 fusion proteins as produced according to Example 7-9 of the present invention.

Chain 1 of Fel d1: The term "chain 1 of Fel d1", as used herein, refers to a polypeptide comprising or alternatively consisting of an amino acid sequence as of SEQ ID NO:30 or a homologous sequence thereof. The term "homologous sequence of SEQ ID NO:30", as used herein, refers to a polypeptide that has an identity to SEQ ID NO:30 which is greater than 80%, more preferably greater than 90%, and even more preferably greater than 95%. The term "chain 1 of Fel d1", as used herein, should also refer to a polypeptide encompassing at least one post-translational modification, including but not limited to at least one glycosylation, of chain 1 of Fel d1, as defined herein. Preferably the chain 1 of Fel d1, as defined herein, consists of at most 130, even more preferably at most 100 amino acids in total.

Chain 2 of Fel d1: The term "chain 2 of Fel d1", as used herein, refers to a polypeptide comprising or alternatively consisting of an amino acid sequence as of SEQ ID NO:31, SEQ ID NO:32 or SEQ ID NO:33, or a homologous sequence thereof. The term "homologous sequence of SEQ ID NO:31, SEQ ID NO:32 or SEQ ID NO:33, as used herein, refers to a polypeptide that has an identity to SEQ ID NO:31, SEQ ID NO:32 or SEQ ID NO:33 which is greater than 80%, more preferably greater than 90%, and even more preferably greater than 95%. The term "chain 2 of Fel d1", as used herein, should also refer to a polypeptide encompassing at least one post-translational modification, including but not limited to at least one glycosylation, of chain 2 of Fel d1, as defined herein Preferably the chain 2 of Fel d1, as defined herein, consists of at most 150, even more preferably at most 130, still more preferably at most 100 amino acids in total.

Immune complex: The term "immune complex", as used herein, refers to a complex formed from the binding of antibody to its cognate/specific antigen. Preferably, the term "immune complex", as used herein, refers to a complex formed from the non-covalent binding of antibody to its cognate/specific antigen. Further preferably, the term "immune complex", as used herein, refers to a complex formed from the binding, preferably the non-covalent binding, of Fel d1-antibody to Fel d1.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the Fel d1 protein, and to which the first attachment site may be linked. The second attachment site of the Fel d1 protein preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" or "Fel d1 protein with at least one second attachment site" refers, therefore, to a construct comprising the Fel d1 protein and at least one second attachment site. However, in particular for a second attachment site, which is not naturally occurring within the Fel d1 protein, such a construct typically and preferably further comprises a "linker". In another preferred embodiment the second attachment site is associated with the Fel d1 protein through at least one covalent bond, preferably through at least one peptide bond. In a further embodiment, the second attachment site is naturally occurring within the Fel d1 protein. In another further preferred embodiment, the second attachment site is artificially added to the Fel d1 protein through a linker, wherein said linker comprises or alternatively consists of a cysteine. Preferably, the linker is fused to the Fel d1 protein by a peptide bond.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the Fel d1 protein or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Association of the linker with the Fel d1 protein is preferably by way of at least one covalent bond, more preferably by way of at least one peptide bond.

Thus, in a first aspect, the present invention provides for an use of a composition in a method of reducing the allergenicity of a cat, wherein an effective amount of said composition is administered to said cat, and wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site. Preferably, said method is a non-therapeutic method of reducing the allergenicity of said cat. In a further preferred embodiment, said cat is not suffering from an allergy or an auto-immune disease, preferably wherein said cat is not suffering from an allergy or an auto-immune disease caused by Fel d1.

In a preferred embodiment, said reducing the allergenicity of said cat, typically and preferably for a human, is effected by generating immune complexes formed of Fel d1 and Fel d1-antibodies in the saliva, the fur, the skin or the tears of said cat, preferably in the saliva of said cat, and wherein preferably said administration of said composition leads to said generating of said immune complexes in the saliva, fur, skin or tears of said cat, preferably in the saliva of said cat.

The reduction of the allergenicity of said cat for a human caused by the administration of the inventive compositions to said cat can further be determined by way of degranulation of basophils from cat allergic patients as described in the examples. Thus, In a preferred embodiment, said reducing the allergenicity of said cat for a human, is reducing the allergenicity of the Fel d1 shed by said cat, and wherein preferably said reducing the allergenicity of the Fel d1 shed by said cat is reducing the allergenicity of the Fel d1 in the saliva, the fur, the skin or the tears of said cat, preferably in the saliva of said cat.

In a preferred embodiment, said administering of said effective amount of the composition to the cat comprises repeated administrations of said effective amount of the composition to the cat, and wherein said repeated administrations are effected in intervals of 2, 3, 4, 8, 12 weeks, and wherein preferably said repeated administrations comprise 2, 3, 4 or 5 administrations of said effective amount of the composition to the cat.

In a further preferred embodiment, said repeated administrations are three administrations effected in intervals of 3 or 4 weeks. Typically and preferably said administering of said effective amount of the composition to the cat further comprises a single administration of said effective amount of the composition to the cat, wherein said single administration is effected 6, 9, 12, 15 or 18 months, preferably 12 months, after the last of said repeated administrations.

Typically, said reduction of said allergically active Fel d1 in the saliva, fur, skin or tears of said cat, preferably in the saliva of said cat, is present at least between one month and 3 months after the last of said repeated administrations.

In a further very preferred embodiment, said reducing the allergenicity of said cat is reducing the allergenicity of said cat for a human exposed to said cat. In a further very preferred embodiment, said reducing the allergenicity of said cat for said human exposed to the cat is (i) reducing the level or severity of the allergic response generated by said human, or (ii) reducing at least one allergic symptom of said human; and wherein preferably said exposure of said human to said cat is the exposure of said human to the saliva, fur, skin or tears of said cat, preferably to the saliva of said cat.

In a further very preferred embodiment, said reducing the allergenicity of said cat is reducing the allergenicity of said cat for a human exposed to said cat, wherein said reducing the allergenicity of said cat for said human exposed to the cat is (i) reducing the level or severity of the allergic response generated by said human, or (ii) reducing at least one allergic symptom of said human; and wherein preferably said exposure of said human to said cat is the exposure of said human to the saliva, fur, skin or tears of said cat, preferably to the saliva of said cat. Preferably, (i) said reduction in the level or severity of the allergic response generated by said human, or (ii) said reduction of said at least one allergic symptom of said human, is expressed by a less positive symptom score test, skin prick test, nasal provocation test or conjunctival provocation test, preferably by a less positive symptom score test or skin prick test, wherein preferably the saliva, fur, skin or tears from said cat before and after said administration, further preferably the saliva from said cat before and after said administration, is used for said skin prick test, nasal provocation test or conjunctival provocation test, preferably said symptom score test or said skin prick test. It is known to the skilled person in the art that allergy and allergic symptoms can be assessed using a symptom score test, skin prick test, a nasal provocation test, a conjunctival provocation test or a bronchial provocation test. These procedures, questionnaires and tests are well-known to the skilled in the art. The term "less positive" as used herein and in the context of a symptom score test, skin prick test, a nasal provocation test, a conjunctival provocation test, and in particular in the context of a symptom score test or a skin prick test refers to a (i) lower or reduced level or severity of the allergic response generated by said human upon exposure to the saliva, fur, skin or tears of said cat, preferably to the saliva of said cat or (ii) lowering or reduction of at least one allergic symptom of said human upon exposure to said cat, preferably upon exposure to the saliva, fur, skin or tears of said cat, preferably to the saliva of said cat, and more preferably upon exposure to the saliva of said cat.

In one embodiment, said virus-like particle is derived from a virus being non-pathogenic to said cat. In a preferred embodiment, said virus-like particle (VLP) is derived from a plant virus or a bacteriophage, and wherein preferably said bacteriophage is derived from a RNA bacteriophage, and wherein further preferably said VLP is derived from a RNA bacteriophage or a plant virus, and again further preferably wherein said VLP is derived from a plant virus. In another preferred embodiment, said VLP is a recombinant VLP, and wherein preferably said recombinant VLP is derived from a plant virus. In another preferred embodiment, said VLP is a VLP of cucumber mosaic virus (CMV). In another preferred embodiment, said VLP is a VLP of an RNA bacteriophage, preferably said VLP is a recombinant VLP of an RNA bacteriophage. In another preferred embodiment, said virus-like particle is a virus-like particle of an RNA-bacteriophage Q. In another preferred embodiment, said VLP is not a VLP of an RNA bacteriophage, preferably said VLP is not a recombinant VLP of an RNA bacteriophage. In another preferred embodiment, said virus-like particle is not a virus-like particle of an RNA-bacteriophage Qβ.

In a preferred embodiment, said VLP is a modified VLP comprising, essentially consisting of, or alternatively consisting of, at least one modified VLP polypeptide, wherein said modified VLP polypeptide comprises, or preferably consists of, (a) a VLP polypeptide, and (b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%.

In a preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In another preferred embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Typically and preferably, said mutated amino acid sequence and said amino acid sequence to be mutated differ in least one and in at most 11, 10, 9, 8, 7, 6, 5, 4, 3, or 2 amino acid residues, and wherein preferably these differences are selected from (i) insertion, (ii) deletion, (iii) amino acid exchange, and (iv) any combination of (i) to (iii).

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1.

In another preferred embodiment, said CMV polypeptide comprises, or preferably consists of, (i) (a) an amino acid sequence of a coat protein of CMV, wherein said amino acid sequence comprises SEQ ID NO:34, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a further preferred embodiment, said CMV polypeptide comprises, or preferably consists of, (a) an amino acid sequence of a coat protein of CMV, wherein said amino acid sequence comprises SEQ ID NO:34, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:1 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:1; and wherein said amino acid sequence as defined in (a) or (b) in this claim comprises SEQ ID NO:34;

or wherein said amino sequence as defined in (a) or (b) in this claim comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:1 or (b) an amino acid sequence having a sequence identity of at least 90% of SEQ ID NO:1; and wherein said amino sequence as defined in (a) or (b) in this claim comprises SEQ ID NO:34; or wherein said amino sequence as defined in (a) or (b) in this claim comprises an amino acid sequence region, wherein said amino acid sequence region has a sequence identity of at least 90% with SEQ ID NO:34.

In another preferred embodiment, said T helper cell epitope replaces a N-terminal region of said CMV polypeptide. In another preferred embodiment the number of amino acids of said N-terminal region replaced is equal to or lower than the number of amino acids of which said T helper cell epitope consists.

In a further very preferred embodiment, said T helper cell epitope replaces a N-terminal region of said CMV polypeptide, and wherein the number of amino acids of said N-terminal region replaced is equal to or lower than the number of amino acids of which said T helper cell epitope consists. Typically and preferably, said replaced N-terminal region of said CMV polypeptide consists of 5 to 15 consecutive amino acids, preferably of 9 to 14 consecutive amino acids, more preferably of 11 to 13 consecutive amino acids.

In a further very preferred embodiment, said N-terminal region of said CMV polypeptide corresponds to amino acids 2-12 of SEQ ID NO: 1.

In another very preferred embodiment, said T helper cell epitope is a universal T helper cell epitope. In another preferred embodiment, said T helper cell epitope consists of at most 20 amino acids.

In a very preferred embodiment, said Th cell epitope is a PADRE sequence. In a further very referred embodiment, said Th cell epitope comprises, preferably consists of, the amino acid sequence of SEQ ID NO:5. In another very preferred embodiment, said Th cell epitope is a PADRE sequence, and wherein said Th cell epitope comprises, preferably consists of, the amino acid sequence of SEQ ID NO:5.

In another preferred embodiment, said T helper cell epitope is derived from a human vaccine. In a very preferred embodiment, said Th cell epitope is derived from tetanus toxin. In a further very referred embodiment, said Th cell epitope has, preferably consists of, the amino acid sequence of SEQ ID NO:4. In another very preferred embodiment, said Th cell epitope is derived from tetanus toxin, and wherein said Th cell epitope has, preferably consists of, the amino acid sequence of SEQ ID NO:4.

In a very preferred embodiment, said Th cell epitope is a PADRE sequence, and wherein said Th cell epitope comprises, preferably consists of, the amino acid sequence of SEQ ID NO:5; or wherein said Th cell epitope is derived from tetanus toxin, and wherein said Th cell epitope has, preferably consists of, the amino acid sequence of SEQ ID NO:4.

In a very preferred embodiment, said CMV polypeptide comprises, or preferably consists of, an amino acid sequence of a coat protein of CMV, wherein said amino acid sequence comprises, or preferably consists of, SEQ ID NO:1 or an amino acid sequence having a sequence identity of at least 95% of SEQ ID NO:1; and wherein said amino sequence comprises SEQ ID NO:34, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO: 1.

In another very preferred embodiment, said modified CMV polypeptide comprises, preferably consists of, an amino acid sequence of SEQ ID NO:6. In another very preferred embodiment, said modified CMV polypeptide comprises, preferably consists of, an amino acid sequence of SEQ ID NO:7. The use of a composition of any one of the claims 6 to 8, wherein said modified CMV polypeptide comprises, preferably consists of, an amino acid sequence of SEQ ID NO:6 or SEQ ID NO:7.

In a very preferred embodiment, said first attachment site and said second attachment site are linked via at least one covalent non-peptide-bond. In another very preferred embodiment, said first attachment site comprises, or preferably is, an amino group, preferably an amino group of a lysine. In a further very preferred embodiment, said second attachment site comprises, or preferably is, a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sufhydryl group that has been chemically attached to the Fel d1 protein. In a further preferred embodiment only one of said second attachment sites associates with said first attachment site through at least one non-peptide covalent bond leading to a single and uniform type of binding of said Fel d1 protein to said modified virus-like particle, wherein said only one second attachment site that associates with said first attachment site is a sulfhydryl group, and wherein said Fel d1 protein and said modified virus-like particle interact through said association to form an ordered and repetitive antigen array, i.e. an ordered and repetitive array of Fel d1 proteins.

In one preferred embodiment of the invention, the Fel d1 protein is linked to the modified VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the Fel d1 protein, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the Fel d1 protein and the modified VLP upon coupling. Preferred cross-linkers belonging to this class include, for example, SPDP and Sulfo-LC-SPDP (Pierce).

Linking of the Fel d1 protein to the modified VLP by using a hetero-bifunctional cross-linker according to the preferred methods described above, allows coupling of the Fel d1 protein to the modified VLP in an oriented fashion. Other methods of linking the Fel d1 protein to the modified VLP include methods wherein the Fel d1 protein is cross-linked to the modified VLP, using the carbodiimide EDC, and NHS. The Fel d1 protein may also be first thiolated through reaction, for example with SATA, SATP or iminothiolane. The Fel d1 protein, after deprotection if required, may then be coupled to the modified VLP as follows. After separation of the excess thiolation reagent, the Fel d1 protein is reacted with the modified VLP, previously activated with a hetero-bifunctional cross-linker comprising a cysteine reactive moiety, and therefore displaying at least one or several functional groups reactive towards cysteine residues, to which the thiolated Fel d1 protein can react, such as described above. Optionally, low amounts of a reducing agent are included in the reaction mixture. In further methods, the Fel d1 protein is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In very preferred embodiments of the invention, the Fel d1 protein is linked via a cysteine residue, having been added to either the N-terminus or the C-terminus of, or a natural cysteine residue within the Fel d1 protein, to lysine residues of the modified virus-like particle. In a preferred embodiment, the composition of the invention further comprises a linker, wherein said linker associates said Fel d1 protein with said second attachment site, and wherein preferably said linker comprises or alternatively consists of said second attachment site.

In another very preferred embodiment, said composition further comprises a linker, said linker is fused to the C-terminus of said Fel d1 protein. In a very preferred embodiment, said Fel d1 protein comprises chain 1 of Fel d1 and chain 2 of Fel d1, wherein said chain 1 of Fel d1 is associated with chain 2 of Fel d1 by at least one covalent bond.

In a very preferred embodiment, said Fel d1 protein is a Fel d1 fusion protein comprising chain 1 of Fel d1 and chain 2 of Fel d1, wherein chain 1 of Fel d1 and chain 2 of Fel d1 are fused either directly via one peptide bond or via a spacer, which links the N-terminus of one chain with the C-terminus of another chain. Several recombinant fusion proteins of Fel d1 have been described (Vailes L D, et al., J Allergy Clin Immunol (2002) 110:757-762; Gronlund H, et al., J Biol Chem (2003) 278:40144-40151; Schmitz N, et al., J Exp Med (2009) 206:1941-1955; WO2006/097530). In a further preferred embodiment, said Fel d1 protein is a Fel d1 fusion protein comprising chain 1 of Fel d1 and chain 2 of Fel d1, wherein said chain 2 of Fel d1 is fused via its C-terminus to the N-terminus of said chain 1 of Fel d1 either directly via one peptide bond or via a spacer, wherein said spacer consists of an amino acid sequence having 1-20 amino acid residues, wherein preferably said spacer consists of an amino acid sequence having 10-20 amino acid residues. In another very preferred embodiment, said spacer consists of an amino acid sequence of 15 amino acid residues, and wherein preferably said spacer has an amino acid sequence of SEQ ID NO: 17.

In a further very preferred embodiment, said Fel d1 protein is a Fel d1 fusion protein comprising chain 1 of Fel d1 and chain 2 of Fel d1, wherein said chain 1 of Fel d1 is fused via its C-terminus to the N-terminus of said chain 2 of Fel d1 either directly via one peptide bond or via a spacer, wherein said spacer consists of an amino acid sequence having 1-20 amino acid residues, wherein preferably said spacer consists of an amino acid sequence having 10-20 amino acid residues. In another very preferred embodiment, said spacer consists of an amino acid sequence of 15 amino acid residues, and wherein preferably said spacer has an amino acid sequence of SEQ ID NO: 17.

In another very preferred embodiment, said chain 1 of Fel d 1 comprises a sequence of SEQ ID NO:30 or a homologue sequence thereof, wherein said homologue sequence has an identity to SEQ ID NO:30 of greater than 80%, preferably greater than 90%, or even more preferably greater than 95%. Preferably, said chain 1 of Fel d 1 comprises a sequence of SEQ ID NO:30 or a homologue sequence thereof, wherein said homologue sequence has an identity to SEQ ID NO:30 of greater than 90%, or even more preferably greater than 95%.

In another very preferred embodiment, said chain 2 of Fel d 1 comprises a sequence of SEQ ID NO:31, SEQ ID NO:32 or SEQ ID NO:33, or a homologue sequence thereof, wherein said homologue sequence has an identity to SEQ ID NO:31, SEQ ID NO:32 or SEQ ID NO:33 of greater than 80%, preferably greater than 90%, and even more preferably greater than 95%. Further preferably, said chain 2 of Fel d 1 comprises a sequence of SEQ ID NO:31, SEQ ID NO:32 or SEQ ID NO:33, or a homologue sequence thereof, wherein said homologue sequence has an identity to SEQ ID NO:31, SEQ ID NO:32 or SEQ ID NO:33 of greater than 90%, and even more preferably greater than 95%.

In a very preferred embodiment, said Fel d1 protein comprises an amino acid sequence selected from: (a) SEQ ID NO:20; (b) SEQ ID NO:25; (c) SEQ ID NO:26; (d) SEQ ID NO:27; or (e) SEQ ID NO:29. In another very preferred embodiment, said Fel d1 protein comprises, preferably consists of, an amino acid sequence of SEQ ID NO:29. In another very preferred embodiment, said Fel d1 protein comprises, preferably consists of, an amino acid sequence of SEQ ID NO:20. In another very preferred embodiment, said Fel d1 protein comprises, preferably consists of, an amino acid sequence of SEQ ID NO:25. In another very preferred embodiment, said Fel d1 protein comprises, preferably consists of, an amino acid sequence of SEQ ID NO:26. In another very preferred embodiment, said Fel d1 protein comprises, preferably consists of, an amino acid sequence of SEQ ID NO:27.

In another aspect, the present invention provides for a method for reducing the allergenicity of a cat, wherein said method comprises administering an effective amount of said composition to said cat, wherein said composition comprises (i) a virus-like particle with at least one first attachment site; (ii) at least one Fel d1 protein with at least one second attachment site; and wherein said virus-like particle and said Fel d1 protein are linked through said at least one first and said at least one second attachment site. Preferably, said method is a non-therapeutic method of reducing the allergenicity of said cat; wherein preferably said method or said composition is further defined as described herein.

In a further aspect, the present invention provides for a composition comprising (i) a virus-like particle (VLP) with at least one first attachment site; (ii) at least one Fel d1 protein with at least one second attachment site; and wherein said virus-like particle and said Fel d1 protein are linked through said at least one first and said at least one second attachment site, and wherein said Fel d1 protein comprises an amino acid sequence selected from SEQ ID NO:25 or SEQ ID NO:27; and wherein said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said modified CMV polypeptide comprises, preferably consists of, an amino acid sequence of SEQ ID NO:6 or SEQ ID NO:7.

EXAMPLES

Example 1

Isolation and Cloning of a Coat Protein (CP) of Cucumber Mosaic Virus (CMV)

Total RNA from CMV-infected lily leaves was isolated using TRI reagent (Sigma, Saint Louis, USA) in accordance with manufacturer's instructions. For cDNA synthesis, a OneStep RT-PCR kit (Qiagen, Venlo, Netherlands) was used. For amplification of the CMV CP gene, primer sequences were chosen following analysis of CMV sequences from GenBank: CMcpF (CACCATGGACAAATCTGAATCAACCAGTGCTGGT) (SEQ ID NO:8) and CMcpR (CAAAGCTTATCAAACTGGGAGCACCCCAGATGTGGGA) (SEQ ID NO:9); NcoI and HindIII sites are underlined. The corresponding PCR products were cloned into the pTZ57R/T vector (Fermentas, Vilnius, Lithuania). *E. coli* XL1-Blue cells were used as a host for cloning and plasmid amplification. To avoid selecting clones containing PCR errors, several CP gene-containing pTZ57 plasmid clones were sequenced using a BigDye cycle sequencing kit and an ABI Prism 3100 Genetic analyzer (Applied Biosystems, Carlsbad, USA). After sequencing, a cDNA of the CMV CP gene without sequence errors (SEQ ID NO:10) coding for CMV coat protein of SEQ ID NO:1 was then subcloned into the NcoI/HindIII sites of the pET28a(+) expression vector (Novagen, San Diego, USA), resulting in the expression plasmid pET-CMVwt (FIG. 1).

Example 2

Expression of CP of SEQ ID NO:1 in *E. coli* Leading to VLPs of CMV

To obtain CMV VLPs, *E. coli* C2566 cells (New England Biolabs, Ipswich, USA) were transformed with the CMV CP gene-containing plasmid pET-CMVwt. After selection of clones with the highest expression levels of target protein, *E. coli* cultures were grown in 2×TY medium containing kanamycin (25 mg/l) on a rotary shaker (200 rev/min; Infors, Bottmingen, Switzerland) at 30° C. to an OD600 of 0.8-1.0. Then, the cells were induced with 0.2 mM IPTG, and the medium was supplemented with 5 mM MgCl2. Incubation was continued on the rotary shaker at 20° C. for 18 h. The resulting biomass was collected by low-speed centrifugation and was frozen at −20° C. After thawing on ice, the cells were suspended in the buffer containing 50 mM sodium citrate, 5 mM sodium borate, 5 mM EDTA, 5 mM mercaptoethanol (pH 9.0, buffer A) and were disrupted by ultrasonic treatment. Insoluble proteins and cell debris were removed by centrifugation (13,000 rpm, 30 min at 5° C.). The soluble CMV CP protein in clarified lysate was pelleted using saturated ammonium sulfate (1:1, vol/vol) overnight at +4° C. Precipitated proteins were solubilized in the same buffer A (without mercaptoethanol) for 4 h at +4° C. Insoluble proteins were removed by low speed centrifugation (13,000 rpm, 15 min at 4° C.). Soluble CMV CP-containing protein solution was separated from the cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient, and the fractions were analyzed by SDS-PAGE (data not shown). Fractions No. 2 and No. 3 containing recombinant CMV CP were combined and were dialyzed against 200 volumes of the buffer (5 mM sodium borate, 2 mM EDTA, pH 9.0) to remove the sucrose and Triton X-100. After dialysis, CMV CP solution was sterilized by filtration through the 0.2µ filter. Next, CMV CP was concentrated using Type70 rotor (Beckman, Palo Alto, USA) ultracentrifugation through the 20% sucrose "cushion" under sterile conditions (50 000 rpm, 4 h, +5° C.). The concentration of purified CMVwt was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

Figure 2A:
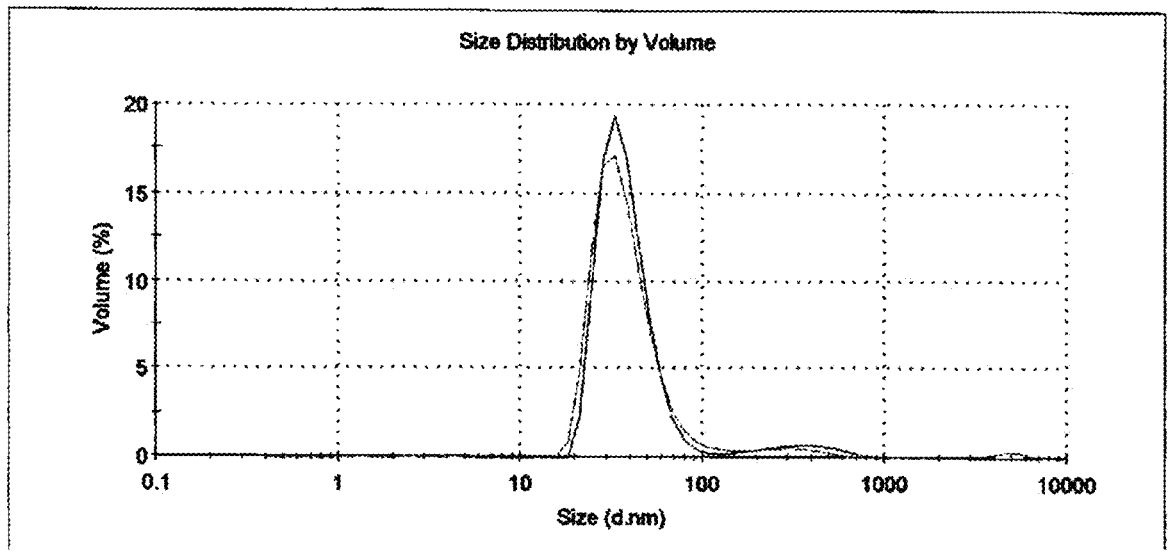
Figure 2B:
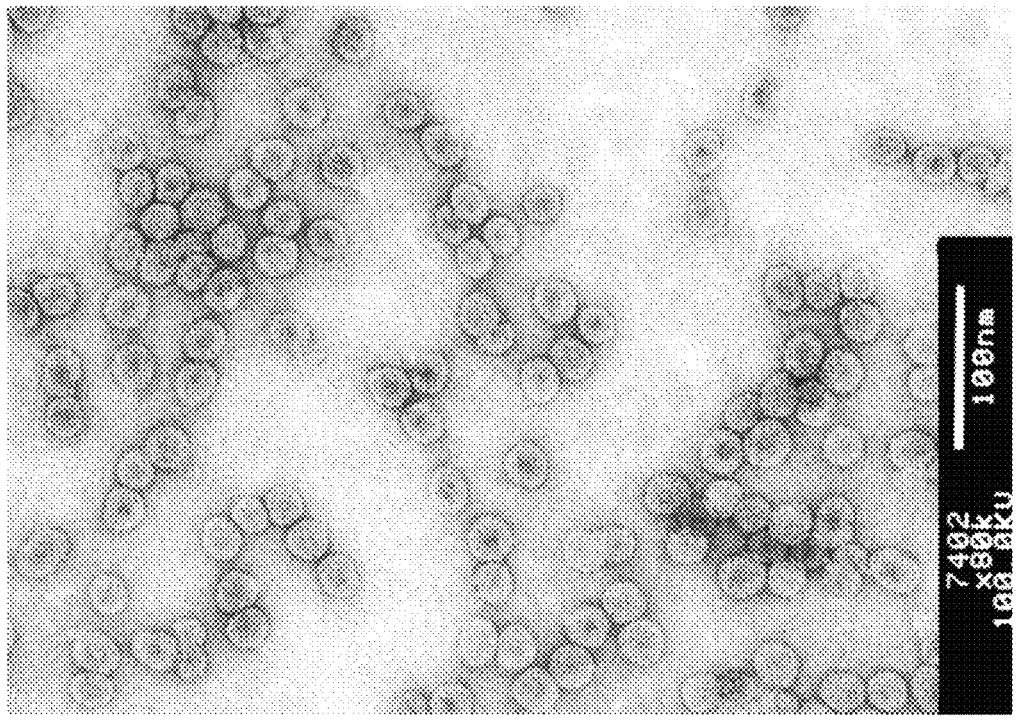

CMV coat protein can be successfully expressed in *E. coli* cells and significant part obtained can be in soluble fraction. Moreover, these proteins are found directly in *E. coli* cell extracts in the form of isometric VLPs, as demonstrated by sucrose gradient analysis (FIG. 2A), dynamic light scattering and electron-microscopy analysis (FIG. 2B).

Example 3

Cloning of a Modified Coat Protein of CMV Containing an Tetanus Toxoid Epitope (CMV-Ntt830)

To replace the original amino acids at the N-terminus of CMV CP of SEQ ID NO:1 with the tetanus toxoid epitope coding sequence, the pET-CMVwt plasmid was used for PCR amplification and mutagenesis. A SalI site located within the CMVwt gene (FIG. 1) was used for cloning the corresponding PCR products.

To introduce the tetanus toxoid epitope coding sequence into the CMVwt gene, a two step PCR mutagenesis was used. For the first step amplification, the following primers were used: pET-220 (AGCACCGCCGCCGCAAGGAA (SEQ ID NO: 11)-upstream from polylinker, the amplified region includes BglII site) and CMV-tt83-1R (ATTTGGAGTTGGCCTTAATATACTGGCCCATGGTATATCTCCTTCTTAAAGT) (SEQ ID NO: 12). For the second round, the PCR product from the first amplification was diluted 1:50 and re-amplified with primers pET-220 (SEQ ID NO:

11) and CMV-tt83Sal-R2 (GACGTCGACGCTCGG-TAATCCCGATAAATTTGGAGTTGGCCT-TAATATACTG) (SEQ ID NO: 13). The resulting PCR product (cDNA of SEQ ID NO: 14 coding for CMV-Ntt830 of SEQ ID NO:6) was subcloned in BglII/SaLI sites of pET-CMVwt. The correct clone was identified by sequencing and designated pET-CMV-Ntt830.

Example 4

Expression of CMV-Ntt830 in *E. coli* Leading to Modified VLPs of CMV

Figure 3A:
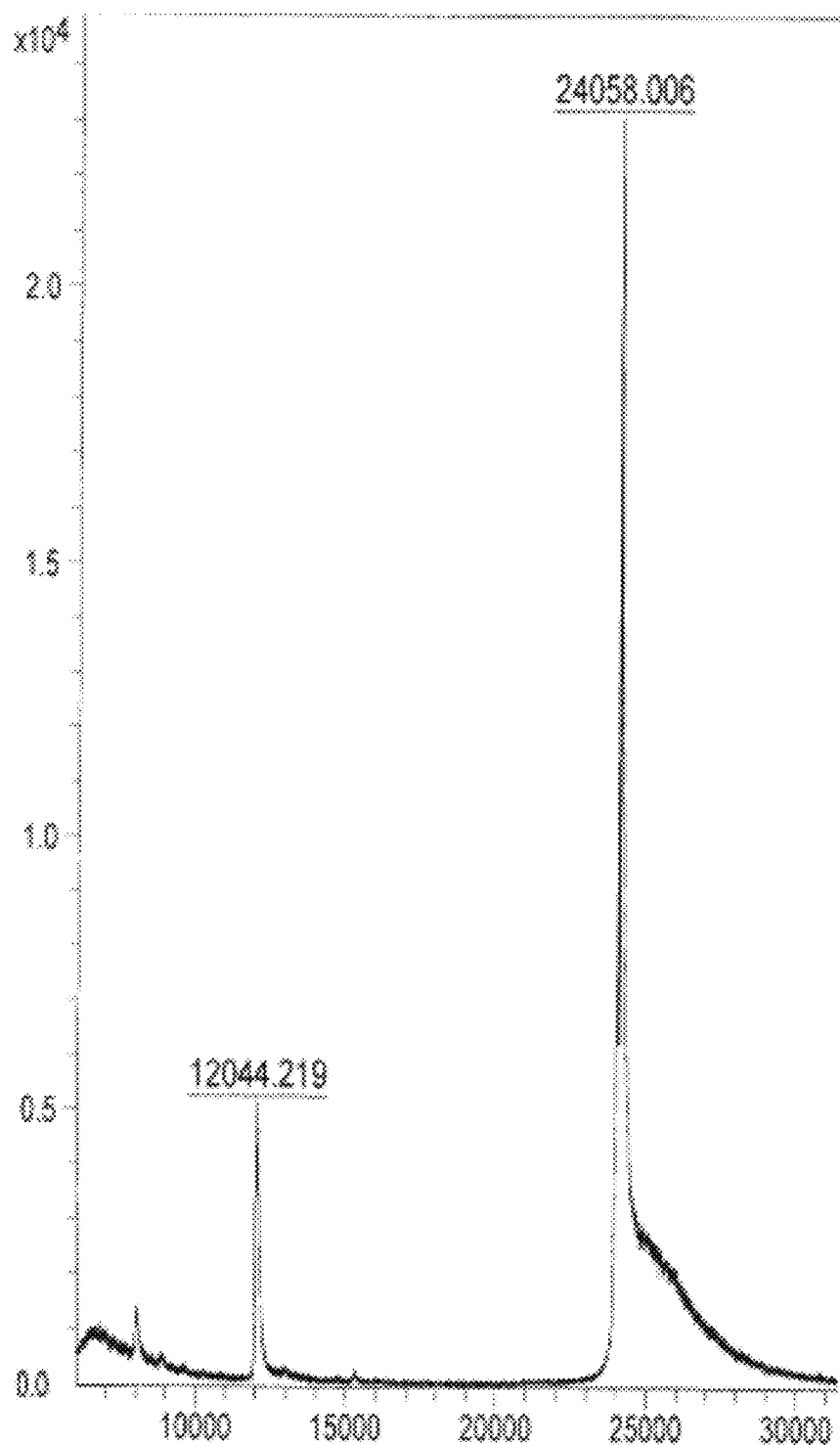
Figure 3B:
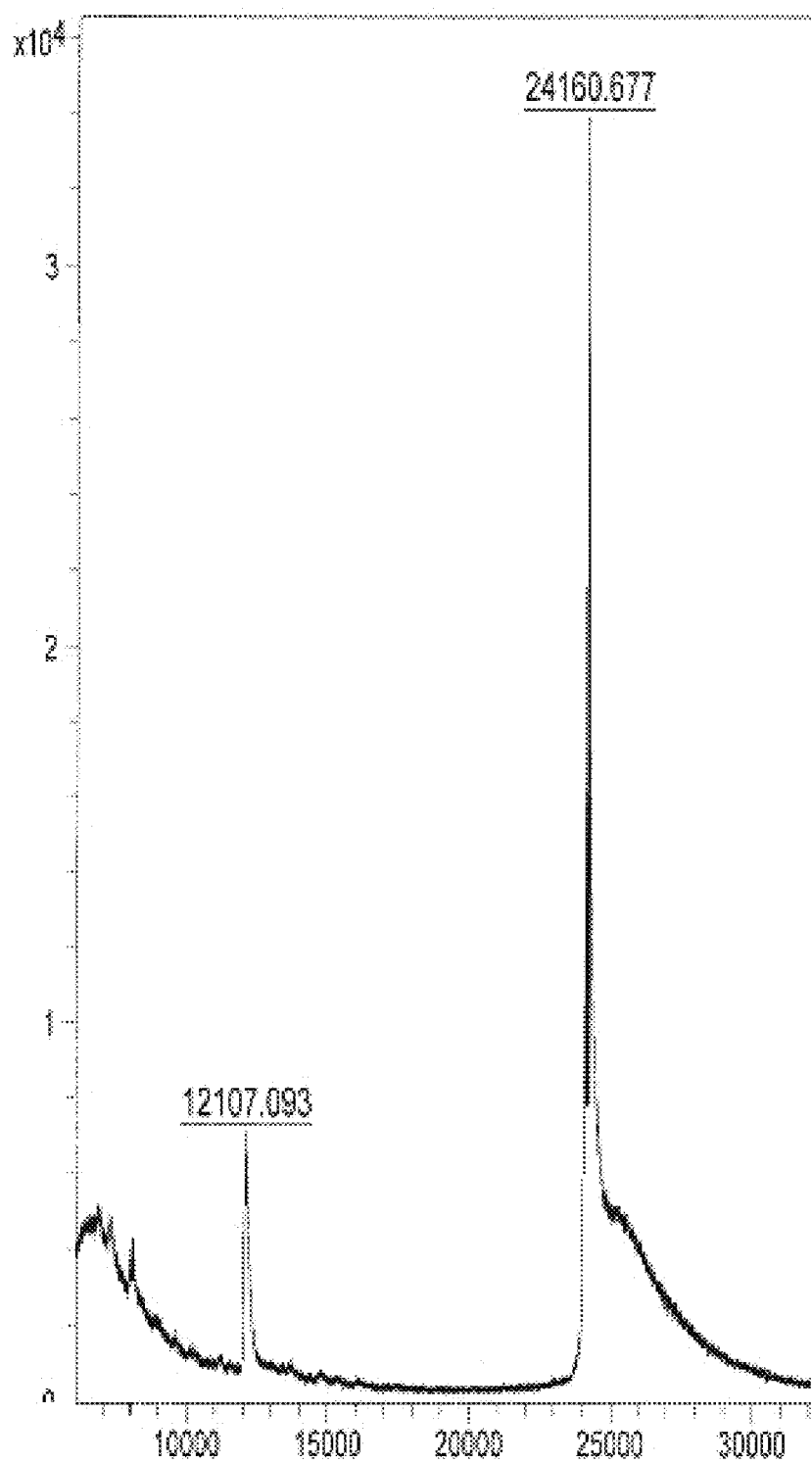
Figure 3C:
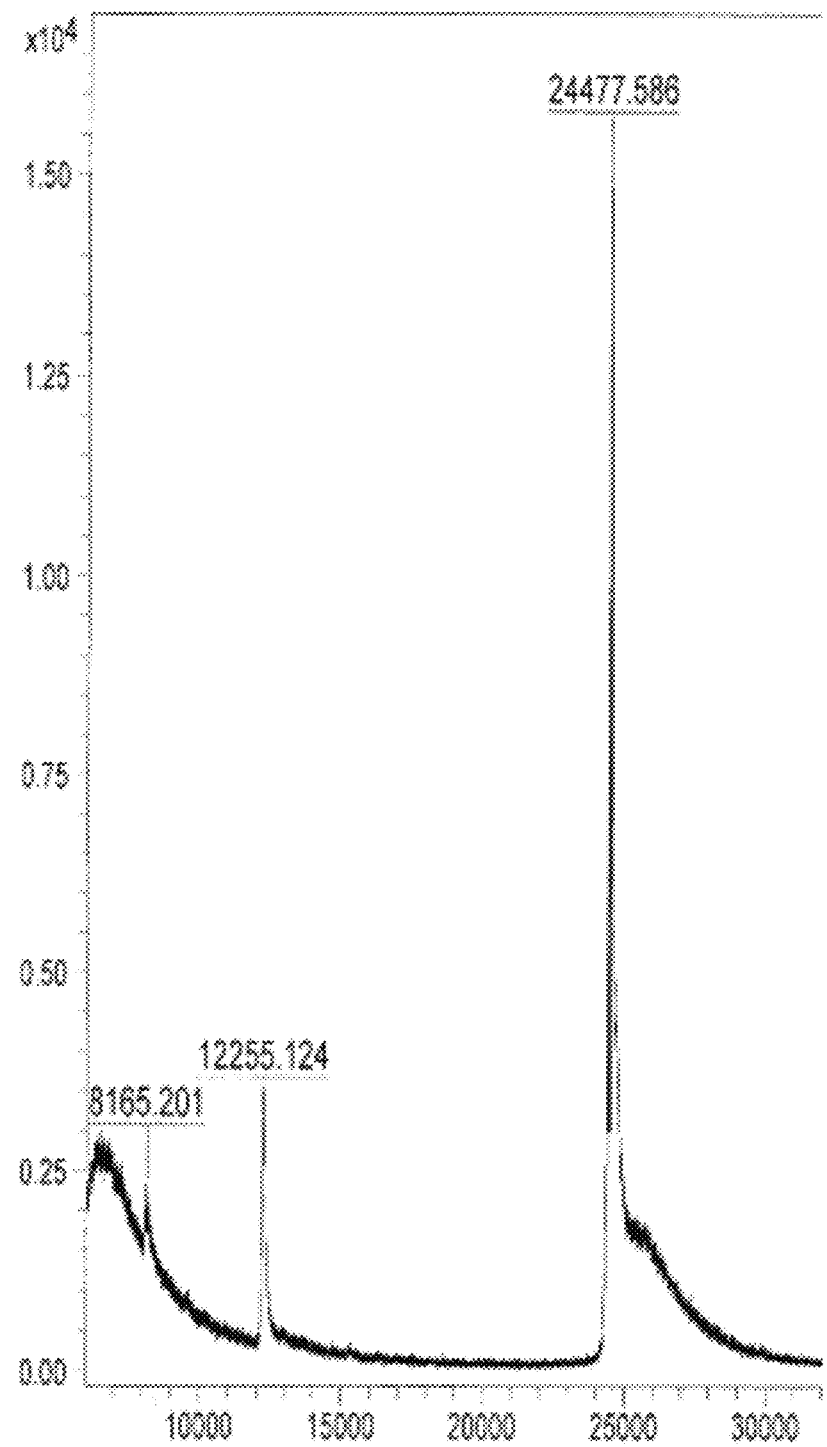

To obtain CMV-Ntt830 VLPs, *E. coli* C2566 cells (New England Biolabs, Ipswich, USA) were transformed with the CMV-Ntt830 gene-containing plasmid pET-CMV-Ntt830. After selection of clones with the highest expression levels of target protein, *E. coli* cultures were grown in 2×TY medium containing kanamycin (25 mg/l) in a rotary shaker (200 rev/min; Infors, Bottmingen, Switzerland) at 30° C. to an OD600 of 0.8-1.0. The, cells were then induced with 0.2 mM IPTG, and the medium supplemented with 5 mM MgCl$_2$. Incubation was continued on the rotary shaker at 20° C. for 18 h. The resulting biomass was collected by low-speed centrifugation and frozen at –20° C. After thawing on ice, the cells were suspended in buffer containing 50 mM sodium citrate, 5 mM sodium borate, 5 mM EDTA, 5 mM mercaptoethanol (pH 9.0, buffer A) and disrupted by sonication. Insoluble proteins and cell debris were removed by centrifugation (13,000 rpm, 30 min at 5° C.). The soluble CMV-Ntt830 protein in clarified lysate was pelleted using saturated ammonium sulfate (1:1, vol/vol) overnight at +4° C. Precipitated proteins were solubilized in the buffer A (without mercaptoethanol) for 4 h at +4° C. Insoluble proteins were removed by low speed centrifugation (13,000 rpm, 15 min at 4° C.). Soluble CMV-Ntt830-containing protein solution was separated from cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient. Fractions containing recombinant CMV-Ntt830 were combined and dialyzed against 200 volumes of 5 mM sodium borate, 2 mM EDTA (pH 9.0) to remove the sucrose and Triton X-100. After dialysis, CMV-Ntt830 solution was sterilized by filtration through a 0.2µ filter. Next, CMV-Ntt830 was concentrated using Type70 rotor (Beckman, Palo Alto, USA) ultracentrifugation through the 20% sucrose "cushion" under sterile conditions (50 000 rpm, 4 h, +5° C.). The concentration of purified CMV-Ntt830 was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels. To demonstrate the presence of the tetanus toxoid epitope in CMV VLPs, mass spectrometric analysis of the purified CMV-Ntt830 VLPs was used. As shown in FIG. 3C, the major peak obtained corresponds to the theoretical molecular mass of the protein if the first methionine is removed which occurs during protein synthesis in *E. coli* cells. Dynamic light scattering and electron microscopy confirmed isometric particle morphology similar to CMVwt VLPs (FIGS. 4A and 4B).

Example 5

Cloning of a Modified Coat Protein of CMV Containing a PADRE Epitope (CMV-Npadr)

To introduce the PADRE epitope coding sequence in CMVwt gene, PCR mutagenesis was carried out using as the template for amplification and subcloning the pET-CMVwt plasmid (see also Example 2 and 3). For the amplification following primers were used: pET-220 (SEQ ID NO: 11) and CMV-padrSal-R (GACGTCGACGCGCGGCCGCCTT-GAGGGTCCACGC GGCCACAAATTTCGCCATGGT) (SEQ ID NO:15). The resulting PCR product (cDNA of SEQ ID NO:16 coding for CMV-Npadr of SEQ ID NO:7) was again subcloned in BglII/SalI sites of pET-CMVwt. The correct clone was identified by sequencing and designated as pET-CMV-Npadr.

Example 6

Expression of CMV-Npadr in *E. coli* Leading to Modified VLPs of CMV

The procedures for expression and purification of CMV-Npadr were essentially the same as for CMV-Ntt830 and are described in Example 4. To demonstrate the presence of the PADRE epitope in CMV VLPs, the mass spectrometric analysis of the purified CMV-Npadr VLPs was used. As shown in FIG. 3B, the major peak obtained corresponds to the theoretical molecular mass of the protein if the first methionine is removed which occurs during protein synthesis in *E. coli* cells. Dynamic light scattering and electron microscopy analysis confirmed isometric particle morphology, (FIG. 5A and FIG. 5B).

Example 7

Cloning of Fel d 1 Fusion Proteins

A Fel d1 fusion protein (named F12H6GGC) consisting of chain 1 of Fel d1 fused to the N-terminus of chain 2 of Fel d1 via a 15 amino acid sequence (GGGGS)$_3$ (SEQ ID NO:17) and incorporating a HHHHHHGGC sequence (SEQ ID NO:18) fused to the C-terminus of chain 2 of Fel d1 was produced by oligonucleotide directed gene synthesis. The corresponding oligonucleotide sequence has the sequence of SEQ ID NO:19, wherein the protein sequence of F12H6GGC has the sequence of SEQ ID NO:20:

MEICPAVKRDVDLFLTGTPDEYVEQVAQYKALPVVLENARILKNCVDAKM

TEEDKENALSVLDKIYTSPLCGGGGSGGGGSGGGGSVKMAETCPIFYDVF

FAVANGNELLLDLSLTKVNATEPERTAMKKIQDCYVENGLISRVLDGLVM

TTISSSKDCMGEAVQNTVEDLKLNTLGRHHHHHHGGC

After synthesis of the gene, it was excised from its helper plasmid and subcloned in frame into NdeI/XhoI sites of the plasmid pET42a(+) (Novagen, USA) resulting in the expression vector pET42-F12H6GGC.

Fel d1 fusion proteins with an additional glycine residue at the C-terminus (named F12H6GGCG) or without a hexa-histidine sequence (named F12GGC) or without a hexa-histidine but with an additional glycine residue at the C-terminus (named F12GGCG) were produced by PCR mutagenesis using the plasmid pET42-F12H6GGC as a template. The oligonucleotide primers used in the PCRs to produce these fusion proteins were:

For F12H6GGCG, the forward primer was Fel_BglF (SEQ ID NO:21) and the reverse primer was Fel6H-cgR (SEQ ID NO:22).

For F12GGC, the forward primer was Fel_BglF (SEQ ID NO:21) and the reverse primer was Feld-dHR (SEQ ID NO:23).

For F12GGCG, the forward primer was Fel_BglF (SEQ ID NO:21) and the reverse primer was Feld-dH-cgR (SEQ ID NO:24).

All PCR products were cut with restriction enzymes BglII/XhoI and subcloned back into vector pET42-F126HGGC at the same excision sites. After isolation of plasmid DNA, the introduced changes were confirmed using a BigDye cycle sequencing kit and an ABI Prism 3100 Genetic analyzer (Applied Biosystems, Carlsbad, USA). The resulting expression vectors were named as pET42-F12H6GGCG, pET42-F12GGC and pET42-F12GGCG. They correspondingly encode the Fel d1 fusion proteins F12H6GGCG (SEQ ID NO: 25), F12GGC (SEQ ID NO: 26) and F12GGCG (SEQ ID NO:27).

(SEQ ID NO: 25)
MEICPAVKRDVDLFLTGTPDEYVEQVAQYKALPVVLENARILKNCVDAKM

TEEDKENALSVLDKIYTSPLCGGGGSGGGGSGGGGSVKMAETCPIFYDVF

FAVANGNELLLDLSLTKVNATEPERTAMKKIQDCYVENGLISRVLDGLVM

TTISSSKDCMGEAVQNTVEDLKLNTLGRHHHHHHGGCG (SEQ ID NO: 26)
MEICPAVKRDVDLFLTGTPDEYVEQVAQYKALPVVLENARILKNCVDAKM

TEEDKENALSVLDKIYTSPLCGGGGSGGGGSGGGGSVKMAETCPIFYDVF

FAVANGNELLLDLSLTKVNATEPERTAMKKIQDCYVENGLISRVLDGLVM

TTISSSKDCMGEAVQNTVEDLKLNTLGRGGC (SEQ ID NO: 27)
MEICPAVKRDVDLFLTGTPDEYVEQVAQYKALPVVLENARILKNCVDAKM

TEEDKENALSVLDKIYTSPLCGGGGSGGGGSGGGGSVKMAETCPIFYDVF

FAVANGNELLLDLSLTKVNATEPERTAMKKIQDCYVENGLISRVLDGLVM

TTISSSKDCMGEAVQNTVEDLKLNTLGRGGCG

The hexa-histidine sequence enables purification by metal chelate affinity chromatography and the C-terminal sequence comprising GGC or GGCG (SEQ ID NO:28) enables coupling of the Fel d1 fusion proteins to CMV-Ntt830 and CMV-Npadr.

Example 8

Expression and Purification of Fel d 1 Fusion Proteins

Expression of Fel d1 Fusion Proteins in *E. coli*.

The Fel d1-expression vectors pET42-F12H6GGC, pET42-F, 12H6GGCG, pET42-F12GGC and pET42-F12GGCG were transformed into *E. coli* C2566 cells (New England Biolabs, Ipswich, USA). Clones expressing the highest levels of target protein were selected and used in further experiments. Expression of the various recombinant Fel d1 fusion proteins was performed in the following way. Cultures of *E. coli* harboring expression plasmids were grown in 2×TY medium containing kanamycin (25 mg/1) on a rotary shaker (200 rev/min; Infors, Bottmingen, Switzerland) at 30° C. to an OD600 of 0.8-1.0. Expression of the Fel d1 fusion protein genes was then induced by adding 0.2 mM IPTG. The medium was supplemented with 5 mM $MgCl_2$. Incubation was continued on a rotary shaker at 20° C. for 18 h. The resulting biomass was collected by low-speed centrifugation and frozen at −20° C. until purification.

Purification of Hexa-Histidine-Tagged Fel d1 Fusion Proteins.

For purification of F12H6GGC and F12H6GGCG fusion proteins, the USB PrepEase Kit (Affymetrix, High Wycombe, UK) was used according to manufacturer's instructions. After thawing on ice, *E. coli* cells from 100 ml culture (approx. 0.75 g) were suspended in 1×LEW buffer containing 5 mM DTT and then disrupted by sonication. Insoluble proteins and cell debris were removed by centrifugation (13,000 rpm, 30 min at 5° C.). The clarified lysate was applied to a Ni-IDA column, washed twice with the same buffer (without DTT) and eluted with 2×1.5 ml of imidazole containing 1×E buffer. The fractions containing Fel d1 were identified by SDS/PAGE (FIG. 6A) and twice dialyzed against 200 volumes of the buffer (20 mM sodium phosphate, 2 mM EDTA, pH 7.0). After dialysis, the protein concentration was estimated using a QuBit fluorometer in accordance with manufacturer's instructions (Invitrogen, Eugene, USA) or by UV spectrophotometric measurement at 280 nm. The identity of the purified proteins was confirmed by mass spectrometric analysis (FIG. 6B) and by Western blot using anti-His-tag antibodies (Novagen, Cat. No. 71840-3; data not shown).

Purification of Fel d1 Fusion Proteins without Hexa-Histidine Tags.

For purification of F12GGC and FG12GGCG fusion proteins, anion exchange and hydrophobic interaction chromatography were used. Three grams of IPTG induced *E. coli* were disrupted by sonication in 20 ml of lysis buffer LB (20 mM Tris/HCl pH 8.0, 50 mM NaCl, 5 mM DTT). After sonication the solution was centrifuged for 15 min at 15 000 g and the supernatant collected. Ammonium sulfate was added with constant stirring until 30% saturation was achieved then incubated for 5 min at RT. After centrifugation, solid ammonium sulfate was added to the recovered supernatant until 50% saturation. After centrifugation, protein pellets were collected and dissolved in 2 ml of LB and excess salt removed with a 5 ml HiTrap™ Desalting Column (GE Healthcare Life Sciences) equilibrated with LB. The desalted protein eluate was loaded onto a 1 ml HiTrap™ Capto™ DEAE column equilibrated with LB. Bound F12GGC or FG12GGCG were eluted with an increasing gradient of NaCl. Fractions containing Fel d1 fusion proteins were collected and pooled. The resulting solution was diluted with 4 volumes of 20 mM Tris/HCl pH 8.0, 5 mM DTT and loaded onto a MonoQ 5/50 GL column in LB and eluted with an increasing NaCl gradient. Fractions containing Fel d1 fusion proteins were collected and pooled. 5 M NaCl was added until a concentration of 2.5 M was reached and DTT added to the solution, to maintain a concentration of 5 mM. The Fel d1 containing solution was then loaded onto a 1 ml HiTrap™ Butyl HP column in 2.5 M NaCl, 5 mM DTT and eluted with a continuously decreasing NaCl concentration. Fractions containing the Fel d1 fusion proteins were collected and pooled. All purification steps were monitored by Coomassie-stained SDS/PAGE gels (FIG. 6C). The identity of purified proteins was confirmed by Western blot using polyclonal antibodies raised against recombinant Fel d1 (data not shown).

Example 9

Authenticity of Recombinant Fel d1 Fusion Protein(s)

Fel d1 Fusion Proteins are Similarly Recognized by Fel d1-Specific Monoclonal Antibodies.

The binding of the Fel d1 fusion protein F12H6GGC and natural Fel d1 (nFel d1) to Fel d1-specific monoclonal antibodies (mAb) was compared using a sandwich ELISA Fel d1 ELISA kit (6F9/3E4) from Indoor biotechnologies (Cardiff, UK). To this end, Nunc ELISA plates were coated with the anti-Fel d1 mAb 6F9 (at 1 microg/ml) at 4° C. overnight. Plates were washed with PBS containing 0.05% Tween 20 (PBST) and blocked with Superblock (Invitrogen) for 2 h at room temperature (RT). Natural Fel d1 as well as F12H6GGC (1 µg/ml) were serially diluted 1:3 and incubated for 2 h at RT. Plates were washed with PBST and biotinylated anti-Fel d1 mAb 3E4 (at 1 µg/ml) was added and incubated for 1 h at RT. Detection utilized Streptavidin conjugated to horse radish peroxidase (HRPO). To this end, plates were washed with PBST then Streptavidin-Peroxidase (Sigma, 1:1000 dilution) was added to the plates for 30 min at RT. Detection was performed with OPD substrate solution and 5% $H_2SO_4$ as stop solution. The absorbance was measured using an ELISA reader (BioRad) at 450 nm.

Natural Fel d1 and F12H6GGC gave similar titers in the ELISA which demonstrates they were similarly recognized by Fel d1-specific mAbs thus confirming the authenticity of the recombinant Fel d1 F12H6GGC (FIG. 7).

Recombinant Fel d1 Fusion Proteins Activate Basophils in Whole Blood of Cat Allergic Patients.

Blood of cat allergic patients contain basophils which carry Fel d1-specific IgE antibodies on their surface which, upon allergen exposure, crosslink the FcεRI and cause degranulation. To check the ability of recombinant Fel d1 to cause degranulation, whole blood from a Fel d1-allergic patients was collected and used in combination with recombinant Fel d1 fusion protein F12H6GGC in a Basophil Activation Test kit of Bühlmann Laboratories (Flow Cast®, FK CCR). This assay measures up-regulation of an exclusive degranulation marker CD63 on CCR3+ basophils. Briefly, 100 µl of stimulation buffer was mixed with 50 µl of EDTA-treated whole blood. In addition, 50 µl of various dilutions of natural Fel d1 or recombinant Fel d1 fusion protein F12H6GGC were added. Positive control solutions including a mAb against FcεRI as well as an unspecific cell activator (fMLP) were also tested in the assay. Staining dye (20 µl per sample), containing anti-CCR3 Ab labeled to PE and anti-CD63 Ab labeled to FITC, was added and incubated at 37° C. for 25 min. Erythrocytes were subsequently lysed adding lysis buffer. After 10 min incubation, the samples were centrifuged at 500×g for 5 min and washed with wash buffer (PBS containing 2% FCS). After a second centrifugation step, the cell pellets were suspended in 200 µl wash buffer and acquired using a flow cytometer (FACS Calibur). The samples were analyzed with Cell Quest Pro software. The percentage of the CD63 expression on CCR3+ basophils was analyzed.

Recombinant Fel d1 fusion proteins was found to readily trigger degranulation of basophils from cat allergic patients. Moreover, when compared to natural Fel d1, similar levels of degranulation were achieved thus demonstrating authenticity of the recombinantly produced Fel d1 fusion proteins. (FIG. 8A/FIG. 8B).

Example 10

Coupling of Fel d1 Fusion Proteins to CMV-Ntt830 and CMV-VLPs

The Fel d1 fusion protein F12H6GGC was covalently linked to CMV-Ntt830 and CMV-Npadr VLPs using the heterobifunctional chemical cross-linker succinimidyl-6-[(β-maleimidopropionamido) hexanoate] (SMPH) in the following way.

CMV-Ntt830 and CMV-Npadr virus-like particles stored in 5 mM Na-borate, 2 mM EDTA buffer, pH 9.0, were subject to buffer exchange with 20 mM Na-phosphate containing 30% sucrose and 2 mM EDTA using PD10 columns (GE Healthcare). A solution of CMV-Npadr or CMV-Ntt830 VLPs reacted for 60 min at RT with 7.5× molar excess of heterobifunctional crosslinker SMPH. Unreacted SMPH was removed with PD10 columns in 20 mM Na-phosphate containing 30% sucrose and 2 mM EDTA.

Fel d1 fusion protein F12H6GGC was treated with 10× molar excess TCEP (Thermo Fisher). Derivatized CMV-Ntt830 and CMV-Npadr-VLPs were reacted with 1× or 2× molar excess of recombinant Fel d1 fusion protein F12H6GGC for 3 h at 23° C. The coupling reaction was analyzed by reducing SDS-PAGE (NuPAGE® 4-12% Bis-Tris gel) stained with Coomassie Blue. Protein bands with masses of approximately 44.5 kDa and 69 kDa were evident after the chemical conjugation reaction (data not shown). These bands correspond to the CMV coat protein (24.5 kDa) covalently linked with the Fel d1 fusion protein F12H6GGC (20 kDa) and two CMV coat protein molecules covalently linked with (49 kDa) one Fel d1 fusion protein F12H6GGC respectively indicating the formation of Fel d1-CMV VLPs. Analogously, further Fel d1 fusion proteins such as the one of SEQ ID NO:25 were covalently linked to CMV-Ntt830 VLPs.

Example 11

Immune Response to Fel d1-CMV VLP in Mice

Groups of three female Balb/c mice were immunized with either Fel d1-CMV-Ntt830-VLP, prepared as described in Example 10, or CMV-Ntt830-VLP simply mixed with Fel d1 fusion protein F12H6GGC. Both compositions contain the same amount of the Fel d1 fusion protein. 10 μg of each composition was prepared in 150 mM PBS, pH 7.4 and injected in a volume of 150 μl intravenously on day 0 and day 14. Mice were bled on days 0 (pre-immune), day 14 and 21, and sera were analyzed by ELISA for natural Fel d1 specific IgG-antibodies.

NUNC ELISA plates were coated with natural Fel d1 (Indoor Biotechnologies) in PBS with a concentration of 1 μg/ml overnight at 4° C. The plates were blocked with Superblock (Invitrogen). A serial dilution of the sera was performed in order to detect OD50. OD50 describes the reciprocal of the dilution, which reaches half of the maximal OD value. IgG-antibodies specific for Fel d1 were detected with an anti-mouse IgG antibody directly labeled to horseradish dish peroxidase (HRPO) (Jackson). The conversion of o-phenylenediamine dihydrochloride (OPD) by the HRPO was measured as color reaction at 450 nm, which was stopped by adding 5% sulfuric acid ($H_2SO_4$) after 7 minutes incubation.

After only a single immunization, Fel d1-specific IgG antibodies were detected in mice (on day 14). The response was boosted by a second injection. Fel d1-CMV VLPs significantly increased the induction of Fel d1 specific IgG antibodies compared to the mixed compositions demonstrating the immune-enhancing effect of chemical conjugation of the Fel d1 fusion proteins to the VLP (FIG. 9).

Example 12

Immune Response to Fel d1-CMV VLPs in Cats

To investigate the immunogenicity and efficacy of Fel d1-CMV-Ntt830 VLP in the target species, female European shorthair cats were immunized 3× (at intervals of 21 days) via the intramuscular route (hind limb) with 100 µg of Fel d1-CMV-Ntt830 VLP formulated in PBS either with adjuvant (15 µg Saponin Matrix M; n=3) or without adjuvant (n=3).

Blood was collected prior to immunization and on days, 22, 43, 58, 71 and 85. After clotting and centrifugation serum samples were stored frozen until assay. Saliva samples were collected from the animals by inserting a sterile swab into the mouth. This was performed prior to immunization and on days 64 and 85.

A. Measurement of IgG Antibody Against (i) Fel d1 and (ii) CMV Carrier in Immunized Cats.

An ELISA assay was used to detect (i) Fel d1 and (ii) CMV specific IgG antibodies in sera from immunized cats. Briefly:

i) Natural Fel d1 (Indoor Biotechnologies), 1 µg/ml in PBS, was applied overnight to NUNC ELISA plates which were then washed and blocked with 2% BSA in PBS Tween 20 (0.05%). After washing, serially diluted cat sera were applied to the plates. After further washing, goat anti-cat IgG antibody labeled with horseradish peroxidase (HRPO) was applied to the plates. Following a final washing step, O-phenylenediamine dihydrochloride (OPD) was added and, after 7 minutes, the reaction was stopped with 5% sulfuric acid. The conversion of OPD by HRPO was measured at 450 nm. The titer is reported as OD50 which is the reciprocal of the dilution which reaches half of the maximal OD value.

Prior to immunization there was no significant anti-Fel d1 IgG. Fel d1-specific IgG was detected on day 22 after a single immunization. After the second immunization on day 22, the response increased further and was maintained at high levels following the third injection administered on day 43. The antibody titers slowly declined thereafter. A similar result was obtained for cats, which had received the Fel d1-CMV-Ntt830 VLP combined with adjuvant (FIG. 10A).

ii) Cucumber mosaic virus-like particle (CMVwt), 1 µg/ml in 0.1 M sodium hydrogen carbonate (pH 9.6), was applied overnight to NUNC ELISA plates. After washing, the plates were blocked with 2% BSA in PBS Tween 20 (0.05%). After washing, serially diluted cat sera were applied to the plates. After further washing, goat anti-cat IgG antibody labeled with HRPO was applied to the plates. Following a final washing step, OPD was added and, after 7 minutes, the reaction was stopped with 5% sulfuric acid. The conversion of OPD by HRPO was measured at 450 nm. The titer is reported as OD50 which is the reciprocal of the dilution which reaches half of the maximal OD value.

Prior to immunization there was no significant anti-CMV IgG. CMV-specific IgG was detected on day 22 after a single immunization. After the second immunization on day 22, the response increased further and was maintained at high levels following the third injection applied on day 43. The antibody titer slowly declined thereafter. A similar result was obtained for cats, which had received the Fel d1-CMV-Ntt830 VLP with adjuvant (FIG. 10B).

B. Determination of Fel d1 and CMV-VLP Specific Antibodies in Saliva Collected from Immunized Cats.

One ml of PBST was pipetted onto the cotton swabs (used to collect saliva) which were incubated at RT for 30 min at 50 rpm on a rotary mixer. The liquid was separated from the swab by centrifugation at 4000 rpm for 10 min using a sieve (cell strainer, BD #352350) in a 50 ml Falcon tube. The flow through was collected and used for ELISA.

To detect anti-Fel d1 IgG and IgA antibodies an indirect ELISA method was used. Briefly, 1 µg/ml of natural Fel d1 in PBS, was applied overnight at 4° C. to NUNC ELISA plates which were then washed and blocked with 2% BSA in PBS Tween 20 (0.05%). After washing, serially diluted (1:3) saliva extracts were applied to the plates which were subsequently washed. For detection of IgG antibodies, goat anti-cat IgG antibody labeled with HRPO was applied. Alternatively, for detection of IgA antibodies, goat anti-cat IgA antibody labeled with HRPO was added to the plates. Following a final washing step, OPD was added and, after 7 minutes, the reaction was stopped with 5% sulfuric acid. The conversion of OPD by HRPO was measured at 450 nm.

Salivary CMV-specific antibodies were similarly measured using recombinantly expressed CMVwt VLP coated ELISA plates.

Following the immunization, Fel d1-specific IgG antibodies (FIG. 11A), above the individual pre-immunization baseline levels, were measured on day 64 from five cats and on day 85 from all six cats. Fel d1-specific IgA antibodies (FIG. 11B), above the individual pre-immunization base-line levels, were measured on day 64 from five cats and on day 85 from five cats. CMV-specific IgG antibodies (FIG. 11C) above pre-immunization base-line levels were measured on day 64 from five cats and on day 85 from five cats. CMV-specific IgA antibodies (FIG. 11D) were measured on day 64 from all six cats and on day 85 from all six cats.

C. Determination of Immune Complexes Consisting of Endogenous Fel d1 and Anti-Fel d1 IgA Antibodies in Saliva Collected from Immunized Cats.

A mixture of three different mAbs (5 µg/ml in PBS), specific for three non-overlapping Fel d1 epitopes, was coated onto NUNC ELISA plates overnight at 4° C. Plates were washed and blocked (2% BSA/PBST) for 2 h at RT. Neat and serially diluted saliva (1:3) extracts were applied to the plates. Immune-complexes comprising endogenous Fel d1 and IgA antibodies were detected with a goat anti-cat IgA Ab-HRPO from AbD Serotec. Following a final washing step, OPD was added and, after 7 minutes, the reaction was stopped with 5% sulfuric acid. The conversion of OPD by HRPO was measured at 450 nm.

Immune complexes consisting of endogenous Fel d1 and IgA antibodies above pre-immunization base-line levels were detected in all cats either on d64 or on d85 (FIG. 12).

Example 13

Saliva Samples from Fel d1-CMV-Ntt830 VLP Immunized Cats Show Reduced Degranulation of Basophils from Cat Allergic Patient The ability of immunization with Fel d1-CMV-Ntt830 VLP to inhibit salivary Fel d1 mediated basophil degranulation was determined using the Basophil activation test as described in Example 9. To this end, saliva samples from cats before and after immunization were collected and extracted as described in Example 12. The Basophil activation test was performed using 50 μl of anti-FcεRI mAb as positive control or 50 μl saliva samples from cats before and after immunization.

Briefly, 100 μl of stimulation buffer was mixed with 50 μl of EDTA-treated whole blood. In addition, 50 μl saliva samples from cats before and after immunization (day 85) or or a mAb against FcεRI as a positive control were added. Staining dye (20 μl per sample), containing anti-CCR3 Ab labeled to PE and anti-CD63 Ab labeled to FITC, was added and incubated at 37° C. for 25 min. Erythrocytes were subsequently lysed adding lysis buffer. After 10 min incubation, the samples were centrifuged at 500×g for 5 min and washed with wash buffer (PBS containing 2% FCS). After a second centrifugation step, the cell pellets were suspended in 200 μl wash buffer and acquired using a flow cytometer (FACS Calibur). The samples were analyzed with Cell Quest Pro software. The percentage of the CD63 expression on CCR3+ basophils was analyzed.

Saliva extracts from 5 of 6 cats taken after immunization on day 85 showed decreased levels of degranulation by up to 20% when compared to saliva extracts before immunization (FIG. 13). When extrapolated to a titration curve constructed with natural Fel d1 in said Basophil activation test and said cat allergic patient, a reduction of 20% in degranulation corresponds to a 13-fold decrease in Fel d1 concentration. This indicates that a significant reduction in allergenic Fel d1 in saliva was achieved.

Example 14

Effect of Cat Immunization Assessed by a Clinical Trial with Cat Allergic Subject A titrated skin prick test of cat allergic human subjects was used to compare the allergenicity of cat fur extracts obtained before and after immunization of cats with Fel d1-CMV-Ntt830 VLP.

Preparation of Cat Fur Extract

Three female European short haired cats were immunized four times subcutaneously with 100 ug of Fel d1-CMV-Ntt830 VLP (prepared as described in Example 10 comprising SEQ ID NO:25) on days 1, 22, 43 and 256. Fur samples from cats were obtained by brushing cats prior to immunization on day 1 and after the fourth immunization on day 312. Collected fur samples were stored frozen until preparation.

In order to prepare fur extracts, 0.03 g of fur were transferred into an extraction vial (1.5 ml tube) and 1 ml of phosphate buffered saline containing 0.05% Tween20 was added to the vial. The extraction tubes were placed into a thermoshaker with a set temperature of 23° C. to incubate at 550 rpm for 1.5 hours. After incubation, the extraction tubes were transferred to a table top Eppendorf centrifuge and spun for 10 min at RT at 16.000×g. The supernatants were transferred into clean 1.5 ml tubes and stored frozen until analysis.

Skin Prick Test

Frozen cat fur extracts (75 μl solution in 0:5 ml Eppendorf tube) were thawed shortly before use and diluted in three-fold serial dilutions with PBS-Tween 20.

The positive allergic statuses of the cat allergic subjects were confirmed using a conventional skin prick test on the lateral side of the left volar forearm with a cat fur extract.

The skin prick test used for patient screening and assessment of cat fur extracts is described briefly. A suitable area of skin was selected for testing, on the volar aspect of the forearms. The skin was clean, dry and free from fat, creams or cosmetics by using rubbing alcohol provided by the cantonal pharmacy. Eczematous or inflamed areas of skin were avoided. The prick sites were marked and numbered using a skin marking pen. The cubital area and wrist were avoided. The vertical and horizontal distance between two allergen extracts was at least 2 cm to avoid cross contamination. A droplet (10 μl) of the cat fur solution was brought onto the skin at the appropriate position utilizing a 20 μl Gilson pipette. The skin prick needle was then pressed through the droplet, pricking the allergen into the dermis. The pressure was applied for approximately one second and the strength of the pressure was sought to be the same for all applications. After 15 minutes the contours of each wheal were encircled using a skin marking pen. These lines were drawn on the red skin surrounding the wheal, without crossing or covering any part of it. It was ensured that no part of the red skin surrounding the wheal appeared inside the encircled part. A copy of the encircled mark was obtained by sticking a transparent self-adhesive tape onto the wheal and then sticking it onto paper to keep a permanent record. The area of the wheal size (mm2) was calculated.

At each patient visit, diluted fur extracts from one cat were tested. Cat fur extracts taken before the immunization was tested on the right arm, cat fur solution of fur taken after the immunization was tested on the left arm.

Results

Seven cat allergic patients (aged 18-65 years, male and female) were included in the single center, open-label clinical study. A comparison of wheal sizes from 16 skin-prick tests (out of a possible 21) that compared pre-immunization and post-immunization fur extracts were successfully obtained.

An analysis of the mean wheal sizes from these 16 skin prick tests shows that fur extracts obtained from immunized cats induced smaller wheal sizes than those collected prior to immunization (FIG. 14). This data suggests cat fur extracts were less allergenic after immunization with Fel d1-CMV-Ntt830 VLP.

The invention claimed is:

1. A method of reducing the allergenicity of a cat for a human exposed to fur of said cat, wherein said method comprises administering an effective amount of a composition to said cat, and wherein said composition comprises
   (i) a virus-like particle (VLP) with at least one first attachment site;
   (ii) at least one Fel d1 protein with at least one second attachment site; and
   wherein said virus-like particle and said Fel d1 protein are linked through said at least one first and said at least one second attachment site wherein said reducing the allergenicity of said cat for said human exposed to said cat is (i) reducing the level or severity of the allergic response generated by said human, or (ii) reducing at least one allergic symptom of said human.

2. The method of claim 1, wherein said reducing the allergenicity of said cat is effected by generating immune complexes formed of Fel d1 and Fel d1-antibodies in the fur of said cat.

3. The method of claim 1 wherein (i) said reduction in the level or severity of the allergic response generated by said human, or (ii) said reduction of said at least one allergic symptom of said human, is expressed by a less positive skin prick test, nasal provocation test or conjunctival provocation test.

4. The method of claim 1, wherein said VLP is a modified VLP comprising at least one modified VLP polypeptide, wherein said modified VLP polypeptide comprises (a) a VLP polypeptide, and (b) a T helper cell epitope, wherein said VLP polypeptide comprises (i) an amino acid sequence of a coat protein of a virus; or (ii) an amino acid having a sequence identity of at least 90% to said coat protein of a virus.

5. The method of claim 1, wherein said VLP is a modified VLP of cucumber mosaic virus (CMV), wherein said modified VLP of CMV comprises at least one modified CMV polypeptide, wherein said modified CMV polypeptide comprises (a) a CMV polypeptide, and (b) a T helper cell epitope; and wherein said CMV polypeptide comprises (ii) an amino acid sequence of a coat protein of CMV; or (ii) an amino acid sequence having a sequence identity of at least 90% to said coat protein of CMV.

6. The method of claim 5, wherein said CMV polypeptide comprises (a) an amino acid sequence of a coat protein of CMV, wherein said amino acid sequence comprises SEQ ID NO:1 or (b) an amino acid sequence having a sequence identity of at least 90% of SEQ ID NO:1; and wherein said amino sequence as defined in (a) or (b) in this claim comprises SEQ ID NO:34; or wherein said amino sequence as defined in (a) or (b) in this claim comprises an amino acid sequence region, wherein said amino acid sequence region has a sequence identity of at least 90% with SEQ ID NO:34.

7. The method of claim 5, wherein said T helper cell epitope replaces a N-terminal region of said CMV polypeptide, and wherein said N-terminal region of said CMV polypeptide comprises amino acids 2-12 of SEQ ID NO:1.

8. The method of claim 5, wherein said T helper cell epitope is a PADRE sequence, and wherein said T helper cell epitope comprises the amino acid sequence of SEQ ID NO:5; or wherein said T helper cell epitope is derived from tetanus toxin, and wherein said T helper cell epitope comprises the amino acid sequence of SEQ ID NO:4.

9. The method of claim 5, wherein said CMV polypeptide comprises an amino acid sequence of a coat protein of CMV, wherein said amino acid sequence comprises SEQ ID NO:1 or an amino acid sequence having a sequence identity of at least 95% of SEQ ID NO:1; and wherein said amino sequence comprises SEQ ID NO:34, and wherein said T helper cell epitope replaces the N-terminal region of said CMV polypeptide, and wherein said replaced N-terminal region of said CMV polypeptide consists of 11 to 13 consecutive amino acids.

10. The method of claim 5, wherein said modified CMV polypeptide comprises an amino acid sequence of SEQ ID NO:6 or SEQ ID NO:7.

11. The method of claim 1, wherein said Fel d1 protein is a Fel d1 fusion protein comprising chain 1 of Fel d1 and chain 2 of Fel d1, wherein chain 1 of Fel d1 and chain 2 of Fel d1 are fused either directly via one peptide bond or via a spacer, which links the N-terminus of one chain with the C-terminus of another chain.

12. The method of claim 1, wherein said Fel d1 protein comprises an amino acid sequence selected from:

(a) SEQ ID NO:20;
(b) SEQ ID NO:25;
(c) SEQ ID NO:26;
(d) SEQ ID NO:27; or
(e) SEQ ID NO:29.

13. The method of claim 2, wherein said administration of said composition leads to said generating of said immune complexes in the saliva, fur, skin or tears of said cat.

14. The method of claim 3, wherein the fur from said cat before and after said administration is used for said skin prick test, nasal provocation test or conjunctival provocation test.

15. The method of claim 4, wherein said VLP polypeptide comprises an amino acid sequence of a coat protein of a plant virus.

16. The method of claim 9, wherein said replaced N-terminal region of said CMV polypeptide consists of 11 consecutive amino acids.

17. The method of claim 16, wherein said N-terminal region of said CMV polypeptide comprises amino acids 2-12 of SEQ ID NO:1.

18. The method of claim 5, wherein said modified CMV polypeptide comprises an amino acid sequence of SEQ ID NO:6.

19. The method of claim 18, wherein said Fel d1 protein comprises an amino acid sequence of SEQ ID NO:25.

20. The method of claim 18, wherein said Fel d1 protein comprises an amino acid sequence of SEQ ID NO:27.

* * * * *